*(12)* United States Patent
Yoshioka et al.

(10) Patent No.: US 10,858,590 B2
(45) Date of Patent: Dec. 8, 2020

(54) COMPOUND, LIQUID CRYSTAL COMPOSITION, OPTICAL FILM, POLARIZING PLATE, AND OPTICAL DISPLAY

(71) Applicant: Sumitomo Chemical Company, Limited, Tokyo (JP)

(72) Inventors: Shinnosuke Yoshioka, Osaka (JP); Noriyuki Hida, Osaka (JP); Katsuaki Miyazaki, Osaka (JP); Daichi Fujimoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 94 days.

(21) Appl. No.: 15/797,067

(22) Filed: Oct. 30, 2017

(65) Prior Publication Data

US 2018/0119015 A1 May 3, 2018

(30) Foreign Application Priority Data

Nov. 1, 2016 (JP) .................................. 2016-214515

(51) Int. Cl.
| | | |
|---|---|---|
| *C09K 19/46* | (2006.01) | |
| *C07D 417/04* | (2006.01) | |
| *C09K 19/56* | (2006.01) | |
| *C07C 69/66* | (2006.01) | |
| *C07C 69/757* | (2006.01) | |
| *C07C 69/78* | (2006.01) | |
| *C07C 69/96* | (2006.01) | |
| *C09K 19/34* | (2006.01) | |
| *C09K 19/38* | (2006.01) | |
| *G02B 5/30* | (2006.01) | |
| *C09K 19/04* | (2006.01) | |
| *G02F 1/1335* | (2006.01) | |
| *H01L 51/52* | (2006.01) | |

(52) U.S. Cl.
CPC .............. *C09K 19/46* (2013.01); *C07C 69/66* (2013.01); *C07C 69/757* (2013.01); *C07C 69/78* (2013.01); *C07C 69/96* (2013.01); *C07D 417/04* (2013.01); *C09K 19/3497* (2013.01); *C09K 19/3823* (2013.01); *C09K 19/56* (2013.01); *G02B 5/3016* (2013.01); *C07C 2601/14* (2017.05); *C07C 2601/16* (2017.05); *C09K 2019/0448* (2013.01); *G02F 1/133528* (2013.01); *G02F 2203/02* (2013.01); *H01L 51/5281* (2013.01)

(58) Field of Classification Search
None
See application file for complete search history.

(56) References Cited

U.S. PATENT DOCUMENTS

| | | | |
|---|---|---|---|
| 7,541,071 B2 | 6/2009 | Shundo et al. | |
| 7,755,728 B2 | 7/2010 | Ichihashi et al. | |
| 8,257,611 B2 | 9/2012 | Uehira et al. | |
| 8,323,527 B2 | 12/2012 | Adlem et al. | |
| 2015/0277006 A1* | 10/2015 | Takasago | C09K 19/2007 349/194 |
| 2016/0075946 A1 | 3/2016 | Ogawa et al. | |
| 2018/0002246 A1 | 1/2018 | Liu et al. | |
| 2018/0208848 A1* | 7/2018 | Archetti | C09K 19/066 |

FOREIGN PATENT DOCUMENTS

| | | | |
|---|---|---|---|
| JP | 2003261470 A | 9/2003 | |
| JP | 200784664 A | 4/2007 | |
| JP | 2007279705 A | 10/2007 | |
| JP | 2010031223 A | 2/2010 | |
| JP | 2011207765 A | 10/2011 | |
| JP | 2013071956 A | * | 4/2013 |
| JP | 2013071956 A | 4/2013 | |
| JP | 2013147607 A | 8/2013 | |
| JP | 2014123134 A | 7/2014 | |
| JP | 201647813 A | 4/2016 | |
| JP | 2016121339 A | 7/2016 | |
| WO | 2014155531 A1 | 10/2014 | |
| WO | 2016114211 A1 | 7/2016 | |

OTHER PUBLICATIONS

English translation of JP2013071956. (Year: 2013).*
"Liquid Crystal Handbook", Liquid Crystal Handbook Editorial Committee, p. 312 (2000).
JP Office Action dated Jan. 23, 2018 in Japanese Application No. 2017-198687.
Office Action dated Apr. 9, 2019 in JP Application No. 2017-198687.

* cited by examiner

*Primary Examiner* — Cynthia H Kelly
*Assistant Examiner* — Anna Malloy
(74) *Attorney, Agent, or Firm* — Panitch Schwarze Belisario & Nadel LLP

(57) ABSTRACT

A compound capable of suppressing the occurrence of alignment defects and lowering the phase transition temperature of a liquid crystal composition without impairing optical characteristics is provided. In particular, a compound represented by formula (A) is provided in which the variable groups are as defined in the specification.

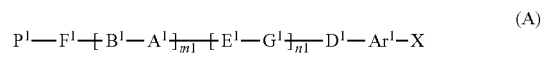

13 Claims, No Drawings

COMPOUND, LIQUID CRYSTAL COMPOSITION, OPTICAL FILM, POLARIZING PLATE, AND OPTICAL DISPLAY

BACKGROUND OF THE INVENTION

Field of the Invention

The present invention relates to a novel compound, a liquid crystal composition containing the compound, a layer containing a cured product of the liquid crystal composition, an optical film including the layer, a polarizing plate, and an optical display.

Description of the Related Art

An optical film such as a retardation film is used for a flat panel display (FPD) device. Such an optical film is obtained, for example, by applying a coating liquid prepared by dissolving a polymerizable liquid crystal compound in a solvent to a supporting substrate and then polymerizing the polymerizable liquid crystal compound. As the polymerizable liquid crystal compound, for example, a nematic liquid crystal compound having a rod-like structure in which two to four 6-membered rings are linked and the like are known (for example, Liquid Crystal Handbook, Liquid Crystal Handbook Editorial Committee, 2000, p. 312).

Meanwhile, the retardation film is required to be polarization convertible in the entire wavelength region, and it is known that uniform polarization conversion is theoretically possible in the wavelength region where [Re(λ)/Re(550)] obtained by dividing the retardation value Re(λ) at a certain wavelength λ by the retardation value Re(550) at 550 nm is closed to 1, and in the wavelength region showing reverse wavelength dispersibility of [Re(450)/Re(550)] of less than 1 and [Re(650)/Re(550)] of larger than 1. As a polymerizable liquid crystal compound that can constitute the retardation film, the compound of JP-A-2011-207765 is known.

SUMMARY OF THE INVENTION

When aligning the polymerizable liquid crystal compound, for example, it is necessary to apply a coating liquid containing a polymerizable liquid crystal compound to a supporting substrate, and then heat it to a temperature higher than the phase transition temperature of the polymerizable liquid crystal compound to undergo a phase transition. Therefore, when the phase transition temperature is high, the supporting substrate is undesirably affected, the usable supporting substrate is restricted, or the heating temperature is increased, so that the production efficiency may be deteriorated in some cases. Furthermore, when an additive is added to the polymerizable liquid crystal compound for the purpose of lowering the phase transition temperature or the like, the molecular alignment of the liquid crystal compound is disturbed by the additive to cause alignment defects, and desired optical characteristics may not be obtained in some cases. In addition, alignment defects are also caused by precipitation of the additive or polymerizable liquid crystal compound as crystals, and desired optical characteristics may not be obtained in some cases.

It is therefore an object of the present invention to provide a compound capable of suppressing the occurrence of alignment defects and lowering the phase transition temperature of a liquid crystal composition without impairing optical characteristics.

DETAILED DESCRIPTION OF THE PREFERRED EMBODIMENTS

In order to solve the above problems, the present inventors have studied in detail for the compound capable of lowering the nematic phase transition temperature of a liquid crystal composition containing a polymerizable liquid crystal compound, and have completed the present invention.

More specifically, the present invention includes the following preferred embodiments.

[1] A compound represented by formula (A).

[Chemical Formula 1]

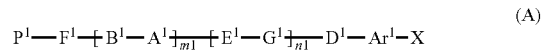

(A)

wherein $B^1$, $E^1$ and $D^1$ each independently represent a single bond or a divalent linking group, $A^1$ and $G^1$ each independently represent a divalent aromatic hydrocarbon group having 6 to 20 carbon atoms or a divalent alicyclic hydrocarbon group having 3 to 16 carbon atoms, the hydrogen atoms contained in the aromatic hydrocarbon group or the alicyclic hydrocarbon group may each independently be substituted with a halogen atom, —$R^1$, —$OR^1$, a cyano group or a nitro group, $R^1$ represents an alkyl group having 1 to 4 carbon atoms, the hydrogen atoms contained in the alkyl group may each independently be substituted with a fluorine atom, the carbon atoms contained in the aromatic hydrocarbon group or the alicyclic hydrocarbon group may each independently be substituted with an oxygen atom, a sulfur atom or a nitrogen atom, $F^1$ represents an alkanediyl group having 1 to 17 carbon atoms, the hydrogen atoms contained in the alkanediyl group may each independently be substituted with a halogen atom, —$R^1$ or —$OR^1$, $R^1$ has the same meaning as described above, —$CH_2$— contained in the alkanediyl group may each independently be substituted with —O—, —S—, —Si— or —CO—, m1 and n1 each independently represent an integer of 0 to 3, $Ar^1$ is a divalent aromatic group which may have a substituent, and contains at least one atom selected from the group consisting of a nitrogen atom, an oxygen atom and a sulfur atom, in the aromatic group, $P^1$ represents a hydrogen atom or a polymerizable group, X represents —OH, —SH, —C(=O)OH, —C(=S)OH, —$NR^2H$ or —$(CH_2)_p$—OH, $R^2$ represents a hydrogen atom or an alkyl group having 1 to 4 carbon atoms, and p represents an integer of 0 to 3.

[2] The compound according to the above [1], wherein $G^1$ is a trans-cyclohexane-1,4-diyl group.

[3] The compound according to the above [1] or [2], wherein $D^1$ is a group represented by formula (C).

[Chemical Formula 2]

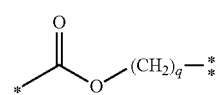

(C)

wherein * represents a linking moiety with $G^1$, ** represents a linking moiety with $Ar^1$, and q represents an integer of 0 to 3.

[4] The compound according to any one of the above [1] to [3], wherein X is —OH or —$(CH_2)_p$—OH.

[5] The compound according to any one of the above [1] to [4], wherein m1 and n1 are 1.

[6] The compound according to any one of the above [1] to [5], wherein $B^1$, $E^1$ and $D^1$ each independently represent a single bond, —$CR^3R^4$—, —$(CH_2)_r$—, —O—, —S—, —CO—O—, —O—CO—, —CO—O—$(CH_2)_r$—, —$(CH_2)_r$—O—CO—, —O—CO—O—, —C(=S)—O—, —O—C(=S)—, —O—C(=S)—O—, —CO—$NR^3$—, —$NR^3$—CO—, —O—$CH_2$—, —$CH_2$—O—, —S—$CH_2$— or —$CH_2$—S—, $R^3$ and $R^4$ each independently represent a hydrogen atom, a fluorine atom or an alkyl group having 1 to 4 carbon atoms, and r represents an integer of 1 to 4.

[7] A liquid crystal composition comprising at least one compound represented by the formula (A) as defined in any one of the above [1] to [6] and at least one polymerizable liquid crystal compound represented by formula (B), wherein the area percentage value of the compound represented by the formula (A) as measured by liquid chromatography is 18% or less based on the sum of area values of the compound represented by the formula (A) and the polymerizable liquid crystal compound represented by the formula (B) contained in the liquid crystal composition.

[Chemical Formula 3]

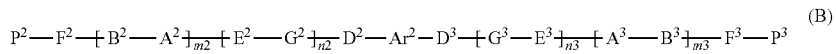
(B)

wherein
$B^2$, $B^3$, $E^2$, $E^3$, $D^2$ and $D^3$ each independently represent a single bond or a divalent linking group, $A^2$, $A^3$, $G^2$ and $G^3$ each independently a divalent aromatic hydrocarbon group having 6 to 20 carbon atoms or a divalent alicyclic hydrocarbon group having 3 to 16 carbon atoms, the hydrogen atoms contained in the aromatic hydrocarbon group or the alicyclic hydrocarbon group may each independently be substituted with a halogen atom, —$R^1$, —$OR^1$, a cyano group or a nitro group, $R^1$ has the same meaning as described above, the carbon atoms contained in the aromatic hydrocarbon group or the alicyclic hydrocarbon group may each independently be substituted with an oxygen atom, a sulfur atom or a nitrogen atom, $F^2$ and $F^3$ each independently represent an alkanediyl group having 1 to 17 carbon atoms, the hydrogen atoms contained in the alkanediyl group may each independently be substituted with a halogen atom, —$R^1$ or —$OR^1$, $R^1$ has the same meaning as described above, —$CH_2$— contained in the alkanediyl group may each independently be substituted with —O—, —S—, —Si— or —CO—, m2, m3, n2 and n3 each independently represent an integer of 0 to 3, $Ar^2$ is a divalent aromatic group which may have a substituent, and contains at least one atom selected from the group consisting of a nitrogen atom, an oxygen atom and a sulfur atom, in the aromatic group, $P^2$ and $P^3$ each independently represent a hydrogen atom or a polymerizable group, and at least one of $P^2$ and $P^3$ is a polymerizable group.

[8] The liquid crystal composition according to the above [7], wherein, in the formula (A) and the formula (B), $B^1$ and $B^2$ and $B^3$ are the same, $E^1$ and $E^2$ and $E^3$ are the same, $D^1$ and $D^2$ and $D^3$ are the same, $A^1$ and $A^2$ and $A^3$ are the same, $G^1$ and $G^2$ and $G^3$ are the same, $F^1$ and $F^2$ and $F^3$ are the same, m1 and m2 and m3 are the same, n1 and n2 and n3 are the same, $Ar^1$ and $Ar^2$ are the same, and $P^1$ and $P^2$ and $P^3$ are the same.

[9] The liquid crystal composition according to the above [7] or [8], further comprising at least one photopolymerization initiator.

[10] A layer containing a cured product of the liquid crystal composition as defined in any one of the above [7] to [9].

[11] An optical film having at least the layer as defined in the above [10].

[12] The optical film according to the above [11], which is a retardation film.

[13] The optical film according to the above [12], which satisfies following formula (I).

$$0.80 \leq Re(450)/Re(550) < 1.00 \quad (I)$$

wherein $Re(\lambda)$ represents a front retardation value for light at a wavelength of λ nm.

[14] A polarizing plate comprising the optical film as defined in any one of the above [11] to [13].

[15] An optical display comprising the polarizing plate as defined in the above [14].

The compound of the present invention can suppress the occurrence of alignment defects and can lower the nematic phase transition temperature of the liquid crystal composition without impairing optical characteristics.

Hereinbelow, the embodiments of the present invention will be described in detail. It should be noted that the scope of the present invention is not limited to the embodiments described herein, and various modifications can be made without departing from the spirit of the present invention.

The compound of the present invention is represented by the following formula (A):

[Chemical Formula 4]

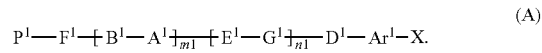
(A)

The compound of the present invention represented by the formula (A) is also referred to as "compound (A)" hereinbelow. The symbols in the formula (A) will be described.

$B^1$, $E^1$ and $D^1$ in the formula (A) each independently represent a single bond or a divalent linking group. The divalent linking group is not particularly limited, and examples thereof include —$CR^3R^4$—, —$(CH_2)_r$—, —O—, —S—, —CO—O—, —O—CO—, —CO—O—$(CH_2)_r$—, —$(CH_2)_r$—O—CO—, —O—CO—O—, —C(=S)—O—, —O—C(=S)—, —O—C(=S)—O—, —CO—$NR^3$—, —$NR^3$—CO—, —O—$CH_2$—, —$CH_2$—O—, —S—$CH_2$— and —$CH_2$—S—. Herein, $R^3$ and $R^4$ each independently represent a hydrogen atom, a fluorine atom or an alkyl group having 1 to 4 carbon atoms, and r represents an integer of 1 to 4.

Examples of the alkyl group having 1 to 4 carbon atoms in $R^3$ and $R^4$ include a methyl group, an ethyl group, a propyl group, an isopropyl group, a butyl group, an isobutyl group, a sec-butyl group, a tert-butyl group and the like, and alkyl groups having 1 to 3 carbon atoms are preferable, alkyl groups having 1 or 2 carbon atoms are more preferable, and a methyl group is still more preferable.

$B^1$ in the formula (A) is preferably —O—, —S—, —O—CO—, —CO—O—, —O—CO—O—, —O—C(=S)—, —O—C(=S)—O—, —O—CH$_2$— or —CH$_2$—O—, and more preferably —O—, —O—CO— or —CO—O—, from the viewpoint of compatibility with a liquid crystal compound.

$D^1$s and $E^1$s in the formula (A) are each independently preferably —O—, —S—, —O—CO—, —CO—O—, —O—CO—O—, —CO—NR$^3$— or —NR$^3$—CO—, and more preferably —O—, —O—CO— or —CO—O—, from the viewpoint of compatibility with a liquid crystal compound.

From the viewpoint of compatibility with a liquid crystal compound, $D^1$ in the formula (A) is still more preferably a group represented by the formula (C):

[Chemical Formula 5]

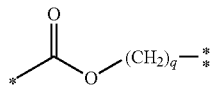

(C)

wherein * represents a linking moiety with $G^1$, ** represents a linking moiety with $Ar^1$, and q represents an integer of 0 to 3.

$A^1$ and $G^1$ in the formula (A) each independently represent a divalent aromatic hydrocarbon group having 6 to 20 carbon atoms or a divalent alicyclic hydrocarbon group having 3 to 16 carbon atoms. The number of carbon atoms of the divalent aromatic hydrocarbon group is preferably 6 to 18, more preferably 6 to 16, still more preferably 6 to 10, and particularly preferably 6. The number of carbon atoms of the divalent alicyclic hydrocarbon group is preferably 4 to 15, more preferably 5 to 10, and further preferably 5 or 6.

The hydrogen atoms contained in the divalent aromatic hydrocarbon group or the divalent alicyclic hydrocarbon group may each independently be substituted with a halogen atom, —R$^1$, —OR$^1$, a cyano group, or a nitro group. Herein, examples of the halogen atom include a fluorine atom, a chlorine atom, a bromine atom, an iodine atom and the like, and a fluorine atom, a chlorine atom or a bromine atom is preferable. R$^1$ represents an alkyl group having 1 to 4 carbon atoms, and the hydrogen atoms contained in the alkyl group may each independently be substituted with a fluorine atom.

Examples of the alkyl group having 1 to 4 carbon atoms include a methyl group, an ethyl group, a propyl group, an isopropyl group, a butyl group, an isobutyl group, a sec-butyl group, a tert-butyl group and the like, and alkyl groups having 1 to 3 carbon atoms are preferable, alkyl groups having 1 or 2 carbon atoms are more preferable, and a methyl group is still more preferable.

Examples of the alkoxy group having 1 to 4 carbon atoms in —OR$^1$ include a methoxy group, an ethoxy group, a propoxy group, an isopropoxy group, a butoxy group, an isobutoxy group, a sec-butoxy group, a tert-butoxy group and the like, and alkoxy groups having 1 to 3 carbon atoms are preferable, alkoxy groups having 1 or 2 carbon atoms are more preferable, and a methoxy group is still more preferable.

The carbon atoms contained in the divalent aromatic hydrocarbon group and the divalent alicyclic hydrocarbon group may each independently be substituted with an oxygen atom, a sulfur atom, or a nitrogen atom. One carbon atom may be substituted with an oxygen atom, a sulfur atom or a nitrogen atom, and two or more carbon atoms may be substituted with two or more atoms selected from the group consisting of an oxygen atom, a sulfur atom and a nitrogen atom. For example, —CH= contained in the divalent aromatic hydrocarbon group may be substituted with —N=. In addition, —CH$_2$— (methylene group) contained in the divalent alicyclic hydrocarbon group may each independently be substituted with —O—, —S—, —NH— or —NR$^1$—, —CH (–)— contained in the alicyclic hydrocarbon group may each independently be substituted with —N(–)—. Herein, R$^1$ has the same meaning as described above.

Examples of the divalent aromatic hydrocarbon group include groups represented by following formulas (a-1) to (a-8). The divalent aromatic hydrocarbon group is preferably a 1,4-phenylene group.

[Chemical Formula 6]

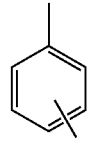

(a-1)

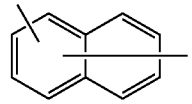

(a-2)

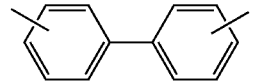

(a-3)

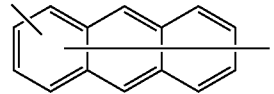

(a-4)

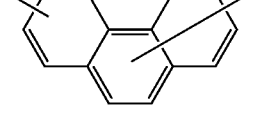

(a-5)

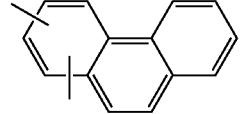

(a-6)

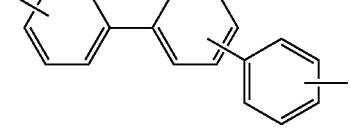

(a-7)

(a-8)

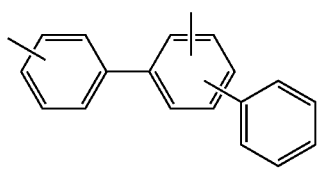

Examples of the divalent alicyclic hydrocarbon group include groups represented by following formulas (g-1) to (g-4). Examples of the divalent alicyclic hydrocarbon group in which —$CH_2$— contained in the alicyclic hydrocarbon group is substituted with —O—, —S—, —NH— or —$NR^1$— include groups represented by following formulas (g-5) to (g-8). Examples of the divalent alicyclic hydrocarbon group in which —CH(-)— contained in the alicyclic hydrocarbon group is substituted with —N(-)— include groups represented by following formulas (g-9) and (g-10). These are preferably 5-membered or 6-membered alicyclic hydrocarbon groups.

[Chemical Formula 7]

(g-1)
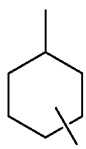

(g-2)
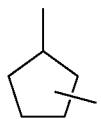

(g-3)
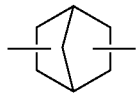

(g-4)
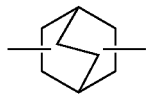

(g-5)
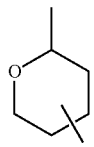

(g-6)
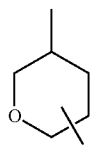

(g-7)
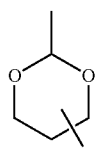

(g-8)
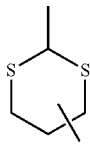

(g-9)
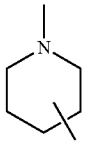

(g-10)
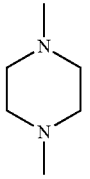

The divalent alicyclic hydrocarbon group is preferably a cycloalkanediyl group represented by the formula (g-1), more preferably a cyclohexane-1,4-diyl group, and still more preferably trans-cyclohexane-1,4-diyl group, from the viewpoint of production of the compound of the present invention.

In one embodiment of the present invention, $A^1$ is preferably a divalent aromatic hydrocarbon group from the viewpoint of production of the compound of the present invention. Further, in one embodiment of the present invention, $G^1$ is preferably a divalent alicyclic hydrocarbon group, more preferably a cyclohexane-1,4-diyl group, and particularly preferably a trans-cyclohexane-1,4-diyl group, from the viewpoint of compatibility with a liquid crystal compound. When $G^1$ is a trans-cyclohexane-1,4-diyl group, it exhibits especially good compatibility.

$F^1$ in the formula (A) represents an alkanediyl group having 1 to 17, preferably 2 to 15, more preferably 3 to 12, even more preferably 4 to 10 carbon atoms. The hydrogen atoms contained in the alkanediyl group may each independently be substituted with —$OR^1$ or a halogen atom. Herein, examples of the halogen atom are as described above, and $R^1$ has the same meaning as described above. —$CH_2$— contained in the alkanediyl group may each independently be substituted with —O— or —CO—.

Examples of the alkanediyl group having 1 to 17 carbon atoms include linear or branched alkanediyl groups or cycloalkanediyl groups having 1 to 17 carbon atoms, a, and the like. The alkanediyl group is preferably a linear alkanediyl group from the viewpoint of production of the compound of the present invention.

m1 and n1 in the formula (A) each independently represent an integer of 0 to 3. Both of m1 and n1 may be 0, and when either one is 0, the other preferably represents an integer of 2 or 3. m1 and n1 are preferably 1 or 2, and more preferably 1. Further, when m1 is 2 or 3, a plurality of $A^1$s and $B^1$s may be the same or different from each other. From the viewpoint that the compound (A) is industrially easily produced, it is preferable that a plurality of $A^1$s and $B^1$s are the same as each other. Also, when n1 is 2 or 3, a plurality of $E^1$s and $G^1$s may be the same or different from each other. From the viewpoint that the compound (A) is industrially easily produced, it is preferable that a plurality of $E^1$s and $G^1$s are the same as each other.

Ar¹ in the formula (A) is a divalent aromatic group which may have a substituent and contains at least one atom selected from the group consisting of a nitrogen atom, an oxygen atom and a sulfur atom in the aromatic group. The divalent aromatic group may contain an aromatic hydrocarbon ring or may contain a heterocyclic ring. Here, in the present invention, the phrase that the divalent aromatic group represented by Ar¹ "contains at least one atom selected from the group consisting of a nitrogen atom, an oxygen atom and a sulfur atom" means that the divalent aromatic group is only required to contain the above hetero atom in Ar¹, and Ar¹ may have a heterocyclic ring or may have no heterocyclic ring. The divalent aromatic group may be monocyclic or polycyclic. Examples of the aromatic hydrocarbon ring which can be contained in the divalent aromatic group represented by Ar¹ include a benzene ring. Examples of the heterocyclic ring which can be contained in the divalent aromatic group represented by Ar¹ include a furan ring, a benzofuran ring, a pyrrole ring, a thiophene ring, a pyridine ring, a thiazole ring, a benzothiazole ring, a phenanthroline ring, and the like. From the viewpoint of optical characteristics, the divalent aromatic group is preferably an aromatic group having a heterocyclic ring. From the same viewpoint, an aromatic group having a benzene ring, a thiazole ring or a benzothiazole ring is more preferable, and an aromatic group having a benzothiazole ring is still more preferable.

The aromatic group represented by Ar¹ preferably has n electrons. The total number $N_\pi$ of the π electrons contained in the aromatic group is preferably 8 or more, more preferably 10 or more, still more preferably 14 or more, and particularly preferably 16 or more, from the viewpoint of easily increasing the expression of reverse wavelength dispersibility of the retardation film obtained from the liquid crystal composition. The total number $N_\pi$ of the π electrons contained in the aromatic group is preferably 30 or less, more preferably 26 or less, and further preferably 24 or less.

Examples of the aromatic group represented by Ar¹ include the following groups.

[Chemical Formula 8]

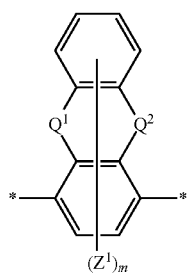
(Ar-1)

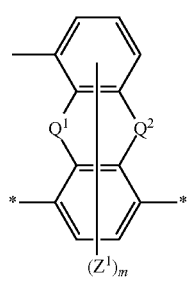
(Ar-2)

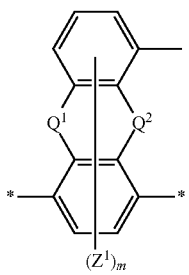
(Ar-3)

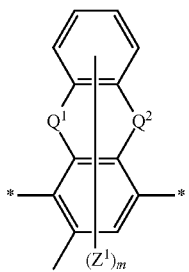
(Ar-4)

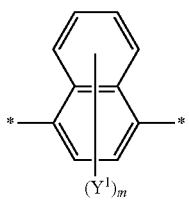
(Ar-5)

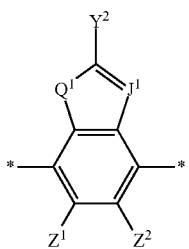
(Ar-6)

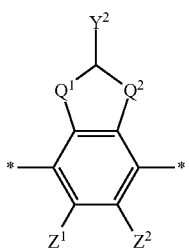
(Ar-7)

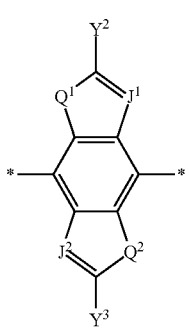
(Ar-8)

-continued
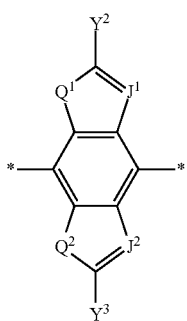
(Ar-9)
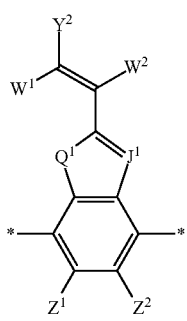
(Ar-10)
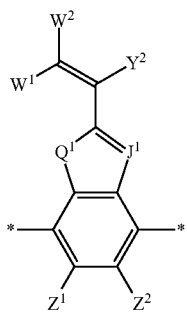
(Ar-11)
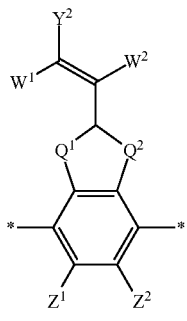
(Ar-12)
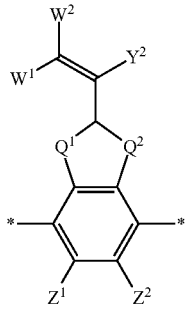
(Ar-13)
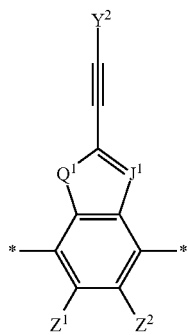
(Ar-14)
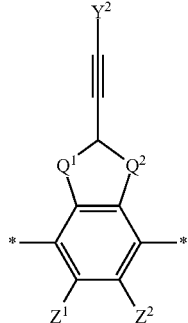
(Ar-15)
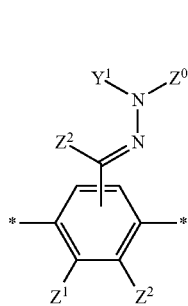
(Ar-16)
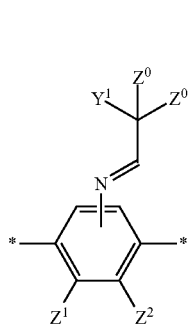
(Ar-17)
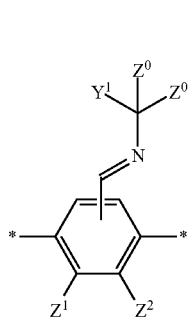
(Ar-18)

-continued

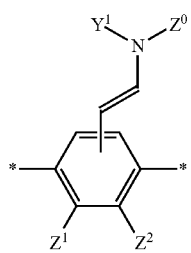
(Ar-19)

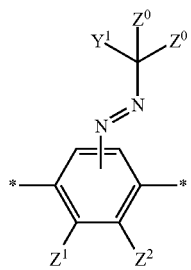
(Ar-20)

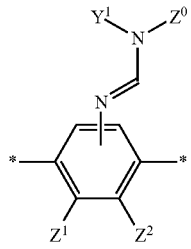
(Ar-21)

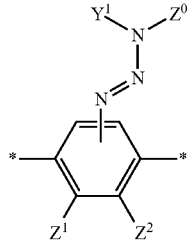
(Ar-22)

In the formulas (Ar-1) to formula (Ar-22), * part represents a linking moiety, and $Z^0$, $Z^1$ and $Z^2$ each independently represent a hydrogen atom, a halogen atom, an alkyl group having 1 to 12 carbon atoms, a cyano group, a nitro group, an alkylsulfinyl group having 1 to 12 carbon atoms, an alkylsulfonyl group having 1 to 12 carbon atoms, a carboxyl group, a fluoroalkyl group having 1 to 12 carbon atoms, an alkoxy group having 1 to 6 carbon atoms, an alkylthio group having 1 to 12 carbon atoms, an N-alkylamino group having 1 to 12 carbon atoms, an N,N-dialkylamino group having 2 to 12 carbon atoms, an N-alkylsulfamoyl group having 1 to 6 carbon atoms, or an N,N-dialkylsulfamoyl group having 2 to 12 carbon atoms.

$Q^1$ and $Q^2$ each independently represent —$CR^5R^6$—, —S—, —$NR^7$—, —CO—, or —O—.

$R^5$, $R^6$ and $R^7$ each independently represent a hydrogen atom or an alkyl group having 1 to 4 carbon atoms.

$J^1$ and $J^2$ each independently represent a carbon atom or a nitrogen atom, and is preferably a nitrogen atom.

$Y^1$, $Y^2$ and $Y^3$ each independently represent an optionally substituted aromatic hydrocarbon group or aromatic heterocyclic group.

$W^1$ and $W^2$ each independently represent a hydrogen atom, a cyano group, a methyl group, or a halogen atom.

m represents an integer of 0 to 6.

Examples of the halogen atom include a fluorine atom, a chlorine atom, a bromine atom, an iodine atom and the like, and a fluorine atom, a chlorine atom or a bromine atom is preferable.

Examples of the alkyl group having 1 to 6 carbon atoms include a methyl group, an ethyl group, a propyl group, an isopropyl group, a butyl group, an isobutyl group, a sec-butyl group, a tert-butyl group, a pentyl group, a hexyl group and the like, and alkyl groups having 1 to 4 carbon atoms are preferable, alkyl groups having 1 or 2 carbon atoms are more preferable, and a methyl group is particularly preferable.

Examples of the alkylsulfinyl group having 1 to 6 carbon atoms include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group, a hexylsulfinyl group and the like, and alkylsulfinyl groups having 1 to 4 carbon atoms are preferable, alkylsulfinyl groups having 1 or 2 carbon atoms are more preferable, and a methylsulfinyl group is particularly preferable.

Examples of the alkylsulfonyl group having 1 to 6 carbon atoms include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, a hexylsulfonyl group and the like, alkylsulfonyl groups having 1 to 4 carbon atoms are preferable, alkylsulfonyl groups having 1 or 2 carbon atoms are more preferable, and a methylsulfonyl group is particularly preferable.

Examples of the fluoroalkyl group having 1 to 6 carbon atoms include a fluoromethyl group, a trifluoromethyl group, a fluoroethyl group, a pentafluoroethyl group, a heptafluoropropyl group, a nonafluorobutyl group and the like, and fluoroalkyl groups having 1 to 4 carbon atoms are preferable, fluoroalkyl groups having 1 or 2 carbon atoms are more preferable, and a trifluoromethyl group is particularly preferable.

Examples of the alkoxy group having 1 to 6 carbon atoms include a methoxy group, an ethoxy group, a propoxy group, an isopropoxy group, a butoxy group, an isobutoxy group, a sec-butoxy group, a tert-butoxy group, a pentyloxy group, a hexyloxy group and the like, and alkoxy groups having 1 to 4 carbon atoms are preferable, alkoxy groups having 1 or 2 carbon atoms are more preferable, and a methoxy group is particularly preferable.

Examples of the alkylthio group having 1 to 6 carbon atoms include a methylthio group, an ethylthio group, a propylthio group, an isopropylthio group, a butylthio group, an isobutylthio group, a sec-butylthio group, a tert-butylthio group, a pentylthio group, a hexylthio group and the like, and alkylthio groups having 1 to 4 carbon atoms are preferable, alkylthio groups having 1 or 2 carbon atoms are more preferable, and a methylthio group is particularly preferable.

Examples of the N-alkylamino group having 1 to 6 carbon atoms include an N-methylamino group, an N-ethylamino group, an N-propylamino group, an N-isopropylamino group, an N-butylamino group, an N-isobutylamino group, an N-sec-butylamino group, an N-tert-butylamino group, an N-pentylamino group, an N-hexylamino group and the like, and N-alkylamino groups having 1 to 4 carbon atoms are preferable, N-alkylamino groups having 1 or 2 carbon atoms are more preferable, and an N-methylamino group is particularly preferable.

Examples of the N,N-dialkylamino group having 2 to 12 carbon atoms include an N,N-dimethylamino group, an N-methyl-N-ethylamino group, an N,N-diethylamino group, an N,N-dipropylamino group, an N,N-diisopropylamino group, an N,N-dibutylamino group, an N,N-diisobutylamino group, an N,N-dipentylamino group, an N,N-dihexylamino group and the like, and N,N-dialkylamino groups having 2 to 8 carbon atoms are preferable, N,N-dialkylamino groups having 2 to 4 carbon atoms are more preferable, and an N,N-dimethylamino group is particularly preferable.

Examples of the N-alkylsulfamoyl group having 1 to 6 carbon atoms include an N-methylsulfamoyl group, an N-ethylsulfamoyl group, an N-propylsulfamoyl group, an N-isopropylsulfamoyl group, an N-butylsulfamoyl group, an N-isobutylsulfamoyl group, an N-sec-butylsulfamoyl group, an N-tert-butylsulfamoyl group, an N-pentylsulfamoyl group, an N-hexylsulfamoyl group and the like, and N-alkylsulfamoyl groups having 1 to 4 carbon atoms are preferable, N-alkylsulfamoyl groups having 1 or 2 carbon atoms are more preferable, and an N-methylsulfamoyl group is particularly preferable.

Examples of the N,N-dialkylsulfamoyl group having 2 to 12 carbon atoms include an N,N-dimethylsulfamoyl group, an N-methyl-N-ethylsulfamoyl group, an N,N-diethylsulfamoyl group, an N,N-dipropylsulfamoyl group, an N,N-diisopropylsulfamoyl group, an N,N-dibutylsulfamoyl group, an N,N-diisobutylsulfamoyl group, an N,N-dipentylsulfamoyl group, an N,N-dihexylsulfamoyl group and the like, N,N-dialkylsulfamoyl groups having 2 to 8 carbon atoms are preferable, N,N-dialkylsulfamoyl groups having 2 to 4 carbon atoms are more preferable, and an N,N-dimethylsulfamoyl group is particularly preferable.

It is preferable that $Z^0$, $Z^1$ and $Z^2$ each independently represent a hydrogen atom, a halogen atom, a methyl group, a cyano group, a nitro group, a carboxyl group, a methylsulfonyl group, a trifluoromethyl group, a methoxy group, a methylthio group, an N-methylamino group, an N,N-dimethylamino group, an N-methylsulfamoyl group, or an N,N-dimethylsulfamoyl group.

Examples of the alkyl group having 1 to 4 carbon atoms in $R^5$, $R^6$ and $R^7$ include a methyl group, an ethyl group, a propyl group, an isopropyl group, a butyl group, an isobutyl group, a tert-butyl group and the like, and alkyl groups having 1 or 2 carbon atoms are preferable, and a methyl group is more preferable.

It is preferable that $Q^1$ and $Q^2$ are each independently —S—, —CO—, —NH—, or —N(CH$_3$)—.

Examples of the aromatic hydrocarbon group in $Y^1$, $Y^2$ and $Y^3$ include aromatic hydrocarbon groups having 6 to 20 carbon atoms such as a phenyl group, a naphthyl group, an anthryl group, a phenanthryl group and a biphenyl group, and a phenyl group or a naphthyl group is preferable, and a phenyl group is more preferable. Examples of the aromatic heterocyclic group include aromatic heterocyclic groups having 4 to 20 carbon atoms having at least one hetero atom such as a nitrogen atom, an oxygen atom and a sulfur atom, such as a furyl group, a pyrrolyl group, a thienyl group, a pyridinyl group, a thiazolyl group and a benzothiazolyl group. Among these, a furyl group, a pyrrolyl group, a thienyl group, a pyridinyl group, a thiazolyl group and a benzothiazolyl group are preferable.

The aromatic hydrocarbon group and the aromatic heterocyclic group may have at least one substituent. Examples of the substituent include halogen atoms, alkyl groups having 1 to 6 carbon atoms, a cyano group, a nitro group, alkylsulfinyl groups having 1 to 6 carbon atoms, alkylsulfonyl groups having 1 to 6 carbon atoms, a carboxyl group, fluoroalkyl groups having 1 to 6 carbon atoms, alkoxy groups having 1 to 6 carbon atoms, alkylthio groups having 1 to 6 carbon atoms, N-alkylamino groups having 1 to 6 carbon atoms, N,N-dialkylamino groups having 2 to 12 carbon atoms, N-alkylsulfamoyl groups having 1 to 6 carbon atoms, N,N-dialkylsulfamoyl groups having 2 to 12 carbon atoms and the like, and halogen atoms, alkyl groups having 1 or 2 carbon atoms, a cyano group, a nitro group, alkylsulfonyl groups having 1 or 2 carbon atoms, fluoroalkyl groups having 1 or 2 carbon atoms, alkoxy groups having 1 or 2 carbon atoms, alkylthio groups having 1 or 2 carbon atoms, N-alkylamino groups having 1 or 2 carbon atoms, N,N-dialkylamino groups having 2 to 4 carbon atoms, and alkylsulfamoyl groups having 1 or 2 carbon atoms are preferable.

Examples of the halogen atoms, alkyl groups having 1 to 6 carbon atoms, a cyano group, a nitro group, alkylsulfinyl groups having 1 to 6 carbon atoms, alkylsulfonyl groups having 1 to 6 carbon atoms, a carboxyl group, fluoroalkyl groups having 1 to 6 carbon atoms, alkoxy groups having 1 to 6 carbon atoms, alkylthio groups having 1 to 6 carbon atoms, N-alkylamino groups having 1 to 6 carbon atoms, N,N-dialkylamino groups having 2 to 12 carbon atoms, N-alkylsulfamoyl groups having 1 to 6 carbon atoms and N,N-dialkylsulfamoyl groups having 2 to 12 carbon atoms include the same as those exemplified above.

Among the formulas (Ar-1) to (Ar-22), the formulas (Ar-6) and (Ar-7) are preferred from the viewpoint of stability of the molecule.

In the formulas (Ar-16) to (Ar-22), $Y^1$ may form an aromatic heterocyclic group together with the nitrogen atom to which it is bonded and $Z^0$. Examples of the aromatic heterocyclic group include those described above as the aromatic heterocyclic ring which Ar may have, and examples thereof include a pyrrole ring, an imidazole ring, a pyrroline ring, a pyridine ring, a pyrazine ring, a pyrimidine ring, an indole ring, a quinoline ring, an isoquinoline ring, a purine ring, a pyrrolidine ring, and the like. The aromatic heterocyclic group may have a substituent. Also, $Y^1$ may be an optionally substituted polycyclic aromatic hydrocarbon group or a polycyclic aromatic heterocyclic group together with the nitrogen atom to which it is bonded and $Z^0$. Examples thereof include a benzofuran ring, a benzothiazole ring, a benzoxazole ring, and the like.

$Y^1$, $Y^2$ and $Y^3$ may each independently be an optionally substituted polycyclic aromatic hydrocarbon group or polycyclic aromatic heterocyclic group. The polycyclic aromatic hydrocarbon group means a condensed polycyclic aromatic hydrocarbon group or a group derived from an aromatic ring assembly. The polycyclic aromatic heterocyclic group refers to a condensed polycyclic aromatic heterocyclic group or a group derived from an aromatic ring assembly. For example, $Y^1$, $Y^2$ and $Y^3$ are each independently preferably any group represented by following formulas ($Y^1$-1) to ($Y^1$-7), and more preferably a group represented by the formula ($Y^1$-1) or ($Y^1$-4).

[Chemical Formula 9]

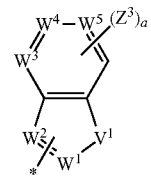

($Y^1$-1)

-continued (Y¹-2)
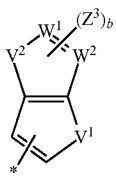

(Y¹-3)
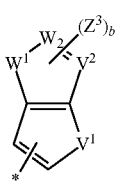

(Y¹-4)
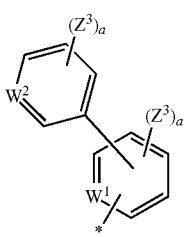

(Y¹-5)
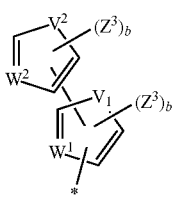

(Y¹-6)
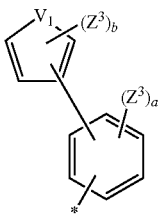

(Y¹-7)
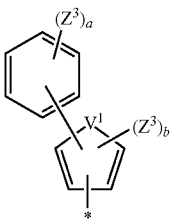

In the formulas (Y¹-1) to (Y¹-7), * part represents a linking moiety, and Z³s each independently represent a halogen atom, an alkyl group having 1 to 6 carbon atoms, a cyano group, a nitro group, a nitroxide group, a sulfone group, a sulfoxide group, a carboxyl group, a fluoroalkyl group having 1 to 6 carbon atoms, an alkoxy group having 1 to 6 carbon atoms, a thioalkyl group having 1 to 6 carbon atoms, an N,N-dialkylamino group having 2 to 8 carbon atoms, or an N-alkylamino group having 1 to 4 carbon atoms.

V¹ and V² each independently represent —CO—, —S—, —NR⁸—, —O—, —Se—, or —SO₂—.

W¹ to W⁵ each independently represent —C= or —N=.

Provided that at least one of V¹, V² and W¹ to W⁵ represents a group containing S, N, O, or Se.

R⁸ represents a hydrogen atom or an alkyl group having 1 to 4 carbon atoms.

as each independently represent an integer of 0 to 3.

bs each independently represent an integer of 0 to 2.

Any group represented by the formulas (Y¹-1) to (Y¹-7) is preferably any group represented by following formulas (Y²-1) to (Y²-16), more preferably any group represented by following formulas (Y³-1) to (Y³-6), and particularly preferably a group represented by the formula (Y³-1) or (Y³-3). In addition, * part represents a linking moiety.

[Chemical Formula 10]

(Y²-1)
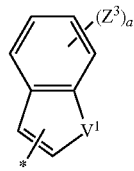

(Y²-2)
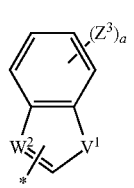

(Y²-3)
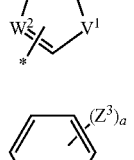

(Y²-4)
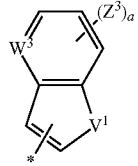

(Y²-5)
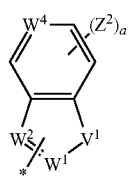

(Y²-6)
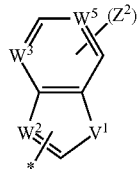

-continued
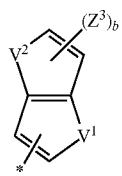 (Y²-7)
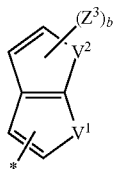 (Y²-8)
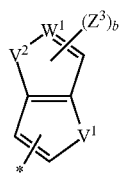 (Y²-9)
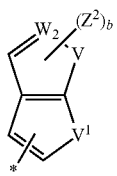 (Y²-10)
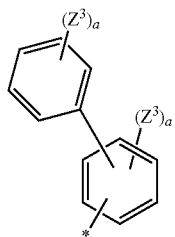 (Y²-11)
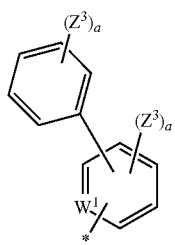 (Y²-12)
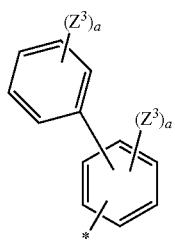 (Y²-13)
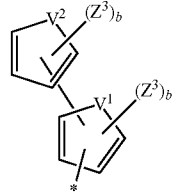 (Y²-14)
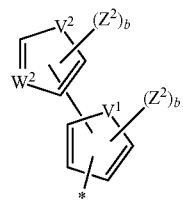 (Y²-15)
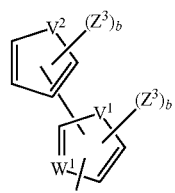 (Y²-16)
In the formulas (Y²-1) to (Y²-16), $Z^3$, a, b, $V^1$, $V^2$ and $W^1$ to $W^5$ have the same meaning as described above.
[Chemical Formula 11]
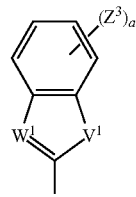 (Y³-1)
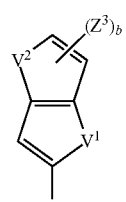 (Y³-2)
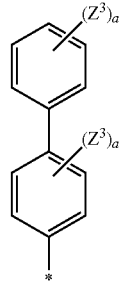 (Y³-3)

-continued

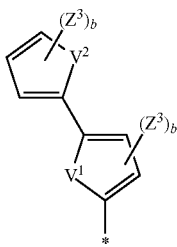
(Y³-4)

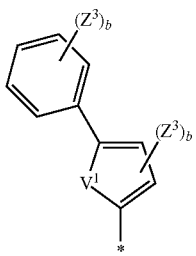
(Y³-5)

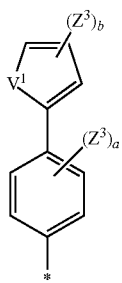
(Y³-6)

In the formulas (Y³-1) to (Y³-6), Z³, a, b, V¹, V² and W¹ have the same meaning as described above.

Examples of Z³ include halogen atoms, alkyl groups having 1 to 6 carbon atoms, a cyano group, a nitro group, alkylsulfinyl groups having 1 to 6 carbon atoms, alkylsulfonyl groups having 1 to 6 carbon atoms, a carboxyl group, fluoroalkyl groups having 1 to 6 carbon atoms, alkoxy groups having 1 to 6 carbon atoms, alkylthio groups having 1 to 6 carbon atoms, N-alkylamino groups having 1 to 6 carbon atoms, N,N-dialkylamino groups having 2 to 12 carbon atoms, N-alkylsulfamoyl groups having 1 to 6 carbon atoms, N,N-dialkylsulfamoyl groups having 2 to 12 carbon atoms, and the like. Among these, halogen atoms, a methyl group, an ethyl group, an isopropyl group, a sec-butyl group, a cyano group, a nitro group, a sulfone group, a nitroxide group, a carboxyl group, a trifluoromethyl group, a methoxy group, a thiomethyl group, an N,N-dimethylamino group and an N-methylamino group are preferable, halogen atoms, a methyl group, an ethyl group, an isopropyl group, a sec-butyl group, a cyano group, a nitro group and a trifluoromethyl group are more preferable, and a methyl group, an ethyl group, an isopropyl group, a sec-butyl group, a pentyl group and a hexyl group are particularly preferable.

Examples of the halogen atoms, alkyl groups having 1 to 6 carbon atoms, alkylsulfinyl groups having 1 to 6 carbon atoms, alkylsulfonyl groups having 1 to 6 carbon atoms, fluoroalkyl groups having 1 to 6 carbon atoms, alkoxy groups having 1 to 6 carbon atoms, alkylthio groups having 1 to 6 carbon atoms, N-alkylamino groups having 1 to 6 carbon atoms, N, N-dialkylamino groups having 2 to 12 carbon atoms, N-alkylsulfamoyl groups having 1 to 6 carbon atoms and N, N-dialkylsulfamoyl groups having 2 to 12 carbon atoms include the same as those exemplified above.

It is preferable that $V^1$ and $V^2$ are each independently —S—, —NR⁸— or —O—.

It is preferable that $W^1$ to $W^5$ are each independently —C= or —N=.

At least one of $V^1$, $V^2$ and $W^1$ to $W^5$ preferably represents a group containing S, N, or O.

a is preferably 0 or 1. b is preferably 0.

Examples of the aromatic group represented by $Ar^1$ also include a group represented by following formula (Ar-23).

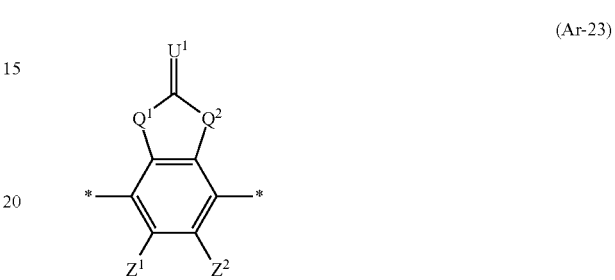
(Ar-23)

In the formula (Ar-23), *, $Z^1$, $Z^2$, $Q^1$ and $Q^2$ have the same meanings as described above, and $U^1$ represents a non-metallic atom of Groups 14 to 16 to which a substituent may bind. Examples of the non-metallic atom of Groups 14 to 16 include carbon atoms, nitrogen atoms, oxygen atoms and sulfur atoms, and preferably include =O, =S, =NR' and =C(R')R', and the like. Examples of the substituent R' include a hydrogen atom, halogen atoms, alkyl groups, halogenated alkyl groups, alkenyl groups, an aryl group, a cyano group, an amino group, a nitro group, a nitroso group, a carboxy group, alkylsulfinyl groups having 1 to 6 carbon atoms, alkylsulfonyl groups having 1 to 6 carbon atoms, fluoroalkyl groups having 1 to 6 carbon atoms, alkoxy groups having 1 to 6 carbon atoms, alkylsulfanyl groups having 1 to 6 carbon atoms, N-alkylamino groups having 1 to 6 carbon atoms, N,N-dialkylamino groups having 2 to 12 carbon atoms, N-alkylsulfamoyl groups having 1 to 6 carbon atoms, dialkylsulfamoyl groups having 2 to 12 carbon atoms and the like, and the two R's in the case where the non-metallic atom is a carbon atom (C) may be the same as or different from each other.

$P^1$ in the formula (A) represents a hydrogen atom or a polymerizable group. The polymerizable group is a group containing a group capable of participating in the polymerization reaction. The group capable of participating in the polymerization reaction is not particularly limited, and examples thereof include a vinyl group, a p-(2-phenylethenyl)phenyl group, an acryloyl group, an acryloyloxy group, a methacryloyl group, a methacryloyloxy group, a carboxyl group, a methylcarbonyl group, a hydroxyl group, a carbamoyl group, alkylamino groups having 1 to 4 carbon atoms, an amino group, a formyl group, —N=C=O, —N=C=S, an oxiranyl group, an oxetanyl group, and the like. From the viewpoint of the reliability of the optical film, $P^1$ is preferably a polymerizable group.

In view of suitability for photopolymerization, the polymerizable group is preferably a radically polymerizable group or a cationically polymerizable group. In particular, an acryloyl group, an acryloyloxy group, a methacryloyl group or a methacryloyloxy group is preferable in view of easy handling and production, and an acryloyl group or an acryloyloxy group is more preferable in view of high polymerizability.

X in the formula (A) represents —OH, —SH, —C(=O)OH, —C(=S) OH, —NR²H or —(CH₂)—OH. Herein, R² represents a hydrogen atom or an alkyl group having 1 to 4 carbon atoms, and p represents an integer of 0 to 3, preferably an integer of 0 to 1. Examples of the alkyl group having 1 to 4 carbon atoms are as described above. X in the formula (A) is preferably —OH or —(CH₂)$_p$—OH from the viewpoint of production of the compound of the present invention.

The compound (A) of the present invention is added to a liquid crystal composition containing a polymerizable liquid crystal compound represented by the following formula (B):

[Chemical Formula 12]

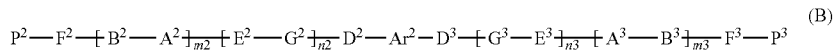

(B)

wherein

B², B³, E², E³, D¹ and D³ each independently represent a single bond or a divalent linking group, A², A³, G² and G³ each independently a divalent aromatic hydrocarbon group having 6 to 20 carbon atoms or a divalent alicyclic hydrocarbon group having 3 to 16 carbon atoms, the hydrogen atoms contained in the aromatic hydrocarbon group or the alicyclic hydrocarbon group may each independently be substituted with a halogen atom, —R¹, —OR¹, a cyano group or a nitro group, R¹ has the same meaning as described above, the carbon atoms contained in the aromatic hydrocarbon group or the alicyclic hydrocarbon group may each independently be substituted with an oxygen atom, a sulfur atom or a nitrogen atom, F² and F³ each independently represent an alkanediyl group having 1 to 17 carbon atoms, the hydrogen atoms contained in the alkanediyl group may each independently be substituted with a halogen atom, —R¹ or —OR¹, R¹ has the same meaning as described above, —CH₂— contained in the alkanediyl group may each independently be substituted with —O—, —S—, —Si— or —CO—, m2, m3, n2 and n3 each independently represent an integer of 0 to 3, Ar² is a divalent aromatic group which may have a substituent, and contains at least one atom selected from the group consisting of a nitrogen atom, an oxygen atom and a sulfur atom, in the aromatic group, P² and P³ each independently represent a hydrogen atom or a polymerizable group, and at least one of P² and P³ is a polymerizable group.

(hereinafter also referred to as "polymerizable liquid crystal compound (B)"), thereby suppressing the occurrence of alignment defects, and lowering the nematic phase transition temperature of the liquid crystal composition without preventing the alignment of the liquid crystal compound too much. Although the reason for this is not clear, the compound (A) of the present invention and the polymerizable liquid crystal compound (B) contained in the liquid crystal composition have structural units similar to each other. Therefore, it is thought that they are compatible with each other, crystals of the compound (A) and the polymerizable liquid crystal compound (B) are hardly precipitated in the liquid crystal composition, and the occurrence of alignment defects is suppressed. In addition, it is considered that, by the state as described above, the nematic phase transition temperature can be lowered without preventing the alignment of the polymerizable liquid crystal compound (B) too much. In particular, from the viewpoint of suppressing the occurrence of alignment defects and easily lowering the phase transition temperature of the liquid crystal composition without impairing the optical characteristics, it is preferable to have the mesogen moiety which is a part other than Ar¹ of the compound (A) of the present invention and the mesogen moiety which is a part other than Ar² of the polymerizable liquid crystal compound (B) have structural units similar to each other.

Next, the symbols in the formula (B) will be described.

B¹, B³, D², D³, E² and E³ in the formula (B) each independently represent a single bond or a divalent linking group. The divalent linking group is not particularly limited, and examples thereof include the groups described for B¹, E¹ and D¹ in the formula (A).

From the viewpoint of easily exhibiting a liquid crystal phase, B² and B³ in the formula (B) are preferably —O—, —S—, —O—CO—, —CO—O—, —O—CO—O—, —O—C(=S)—, —O—C(=S)—O—, —O—CH₂— or —CH₂—O—, and more preferably —O—, —O—CO— or —CO—O—. From the viewpoint that the polymerizable liquid crystal compound (B) can be easily produced and the production cost can be suppressed, it is preferable that B² and B³ are the same as each other. Incidentally, the fact that B² and B³ are the same as each other means that the structures of B² and B³ are the same as each other when viewing Ar as a center, for example, in the case where B² is —O—CO—, B³ which is the same as B² each other is —CO—O—. This also applies to the relationships between D¹ and D², E² and E³, A² and A³, G² and G³, F² and F³, and P² and P³.

From the viewpoint of easily exhibiting a liquid crystal phase, D², D³, E² and E³ in the formula (B) are each independently preferably —O—, —S—, —O—CO—, —CO—O—, —O—CO—O—, —CO—NR³— or —NR³—CO—, and more preferably —O—, —O—CO— or —CO—O—. From the viewpoint that the polymerizable liquid crystal compound (B) can be easily produced and the production cost can be suppressed, it is preferable that D² and D³ and E² and E³ are the same as each other.

A², A³, G² and G³ in the formula (B) each independently represent a divalent aromatic hydrocarbon group having 6 to 20 carbon atoms or a divalent alicyclic hydrocarbon group having 3 to 16 carbon atoms. The number of carbon atoms of the divalent aromatic hydrocarbon group is preferably 6 to 18, more preferably 6 to 16, still more preferably 6 to 10, and particularly preferably 6. The number of carbon atoms of the divalent alicyclic hydrocarbon group is preferably 4 to 15, more preferably 5 to 10, and further preferably 5 or 6.

For the divalent aromatic hydrocarbon group and the divalent alicyclic hydrocarbon group, the description of A¹ and G¹ in the formula (A) applies equally. Herein, A¹ in the formula (A) and A² and A³ in the formula (B) may be the same or different from each other. Also, G¹ in the formula (A) and G² and G³ in the formula (B) may be the same or different from each other. From the viewpoint that the polymerizable liquid crystal compound (B) can be easily produced and the production cost can be suppressed, it is preferable that A² and A³ and G² and G³ are each the same as each other. Also, from the viewpoint of enhancing compatibility between the polymerizable liquid crystal compound (B) and the compound (A) of the present invention and easily suppressing alignment defects, it is preferable that $A^1$ in the formula (A) and $A^2$ and $A^3$ in the formula (B) are the same as each other, and $G^1$ in the formula (A) and $G^2$ and $G^3$ in the formula (B) are the same as each other.

$F^2$ and $F^3$ in the formula (B) each independently represent an alkanediyl group having 1 to 17 carbon atoms, preferably 2 to 15 carbon atoms, more preferably 3 to 12 carbon atoms, and further preferably 4 to 10 carbon atoms. The hydrogen atoms contained in the alkanediyl group may each independently be substituted with —$OR^1$ or a halogen atom. Herein, examples of the halogen atom are as described above, and $R^1$ has the same meaning as described above. —$CH_2$— contained in the alkanediyl group may each independently be substituted with —O— or —CO—. Examples of the alkanediyl group having 1 to 17 carbon atoms include the above-mentioned groups for $F^1$ in the formula (A), and the preferred description concerning $F^1$ equally applies to $F^2$ and $F^3$. From the viewpoint that the polymerizable liquid crystal compound (B) can be easily produced and the production cost can be suppressed, it is preferable that $F^2$ and $F^3$ are the same as each other. Also, from the viewpoint of enhancing compatibility between the polymerizable liquid crystal compound (B) and the compound (A) of the present invention and easily suppressing alignment defects, it is preferable that $F^1$ in the formula (A) and $F^2$ and $F^3$ in the formula (B) are the same as each other.

m2, m3, n2 and n3 in the formula (B) each independently represent an integer of 0 to 3.

All of m2, m3, n2 and n3 may be 0, and when either one of m2 and m3 is 0, the other preferably represents an integer of 2 or 3, and when either of n2 and n3 is 0, the other preferably represents an integer of 2 or 3. m2, m3, n2 and n3 are preferably 1 or 2, and more preferably 1. Also, from the viewpoint that the polymerizable liquid crystal compound (B) can be easily produced and the production cost can be suppressed, it is preferable that m2 and m3, and n2 and n3 are each the same integer. Further, when m2 is 2 or 3, a plurality of $A^2$s and $B^2$s may be the same as or different from each other. From the viewpoint that the polymerizable liquid crystal compound (B) is industrially easily produced, it is preferable that a plurality of $A^2$s and $B^2$s are the same as each other. This also applies to the case where m3 is 2 or 3. Moreover, when n2 is 2 or 3, a plurality of $E^2$s and $G^3$s may be the same as or different from each other. From the viewpoint that the polymerizable liquid crystal compound (B) is industrially easily produced, it is preferable that a plurality of $E^2$s and $G^3$s are the same as each other. This also applies to the case where n3 is 2 or 3. Also, from the viewpoint of enhancing compatibility between the polymerizable liquid crystal compound (B) and the compound (A) of the present invention and easily suppressing alignment defects, it is preferable that m1 in the formula (A) and m2 and m3 in the formula (B) are the same as each other, and n1 in the formula (A) and n2 and n3 in the formula (B) are the same as each other.

$Ar^2$ in the formula (B) is a divalent aromatic group which may have a substituent and contains at least one atom selected from the group consisting of a nitrogen atom, an oxygen atom and a sulfur atom in the aromatic group. As to $Ar^2$, the examples and preferred description given for $Ar^1$ in the formula (A) apply equally. From the viewpoint of enhancing compatibility between the polymerizable liquid crystal compound (B) and the compound (A) of the present invention and easily suppressing alignment defects, it is preferable that $Ar^1$ in the formula (A) and $Ar^2$ in the formula (B) are the same as each other.

The method for producing the compound (A) of the present invention and the polymerizable liquid crystal compound (B) are not particularly limited, and can be produced by combining known organic synthetic reactions described in Methoden der Organischen Chemie, Organic Reactions, Organic Syntheses, Comprehensive Organic Synthesis, "Shin Jikken Kagaku Koza" (New Series of Experimental Chemistry) (For example, condensation reaction, esterification reaction, Williamson reaction, Ullman reaction, Wittig reaction, Schiff base formation reaction, benzylation reaction, Sonogashira reaction, Suzuki-Miyaura reaction, Negishi reaction, Kumada reaction, Hiyama reaction, Buchwald-Hartwig reaction, Friedel-Crafts reaction, Heck reaction, Aldol reaction, etc.) according to its structure, as appropriate.

The compound of the present invention represented by the formula (A) can be produced by performing an esterification reaction of an alcohol compound (D-1) represented by formula (D-1):

[Chemical Formula 13]

HO—$Ar^1$—X     (D-1)

with a carboxylic acid compound (E-1) represented by formula (E-1):

[Chemical Formula 14]

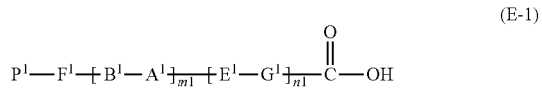

(E-1)

$Ar^1$, X, $P^1$, $F^1$, $B^1$, $A^1$, $E^1$, $G^1$, m1 and n1 in the formulas (D-1) and (E-1) have the same meanings as the symbols in the formula (A), and the preferred description applies equally.

Examples of the carboxylic acid compound (E-1) include following compounds (R-1) to (R-104).

[Chemical Formula 15]

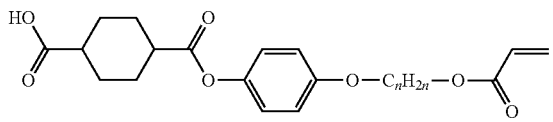
(R-1)

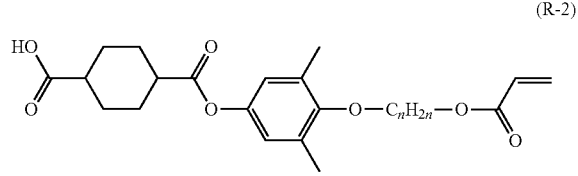
(R-2)

-continued

-continued
(R-21) 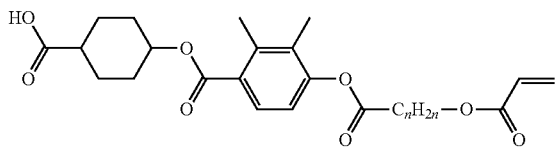
(R-22) 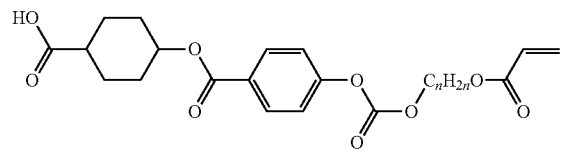
(R-23) 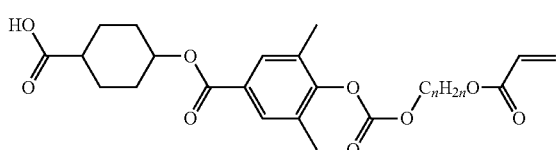
(R-24) 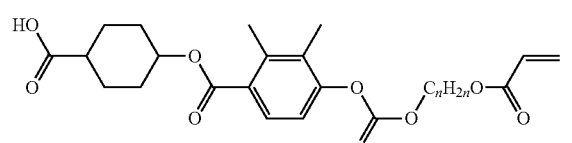
[Chemical Formula 16]
(R-25) 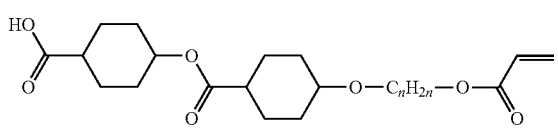
(R-26) 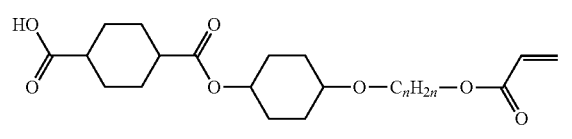
(R-27) 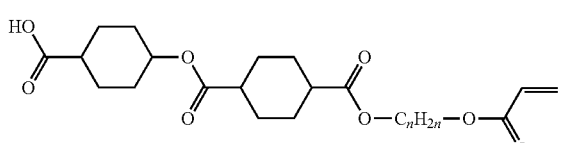
(R-28) 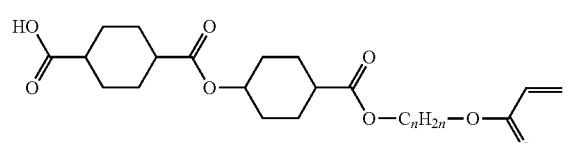
(R-29) 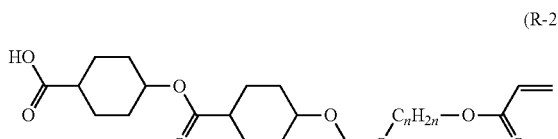
(R-30) 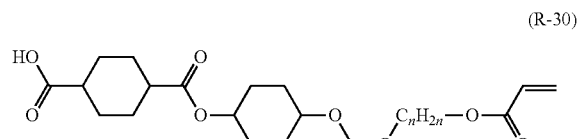
(R-31) 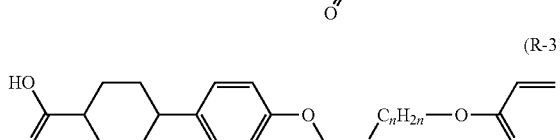
(R-32) 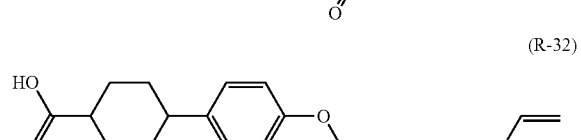
(R-33) 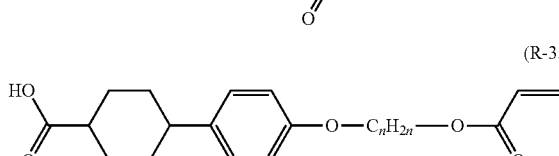
(R-34) 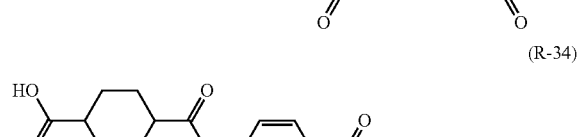
(R-35) 
(R-36) 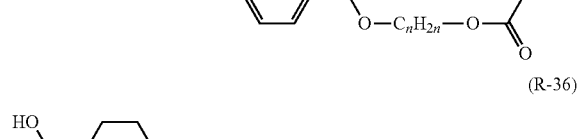
(R-37) 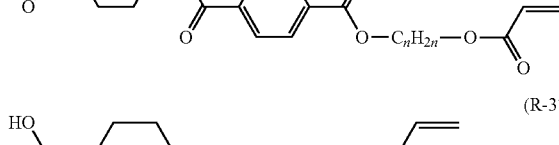
(R-38) 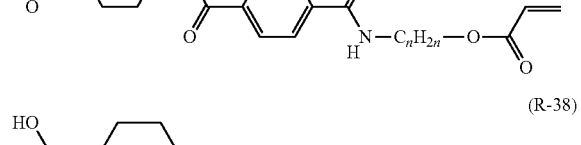
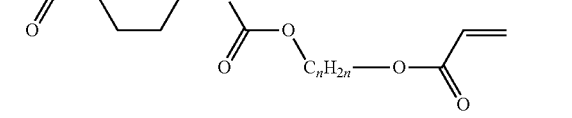

-continued
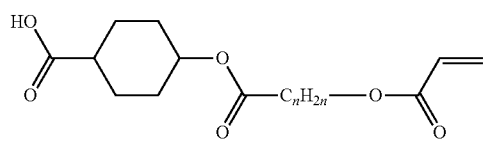
(R-39)
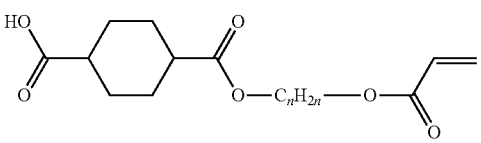
(R-40)
[Chemical Formula 17]
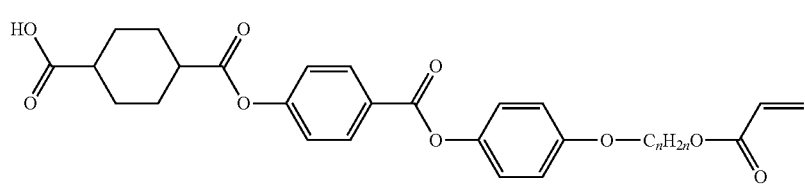
(R-41)
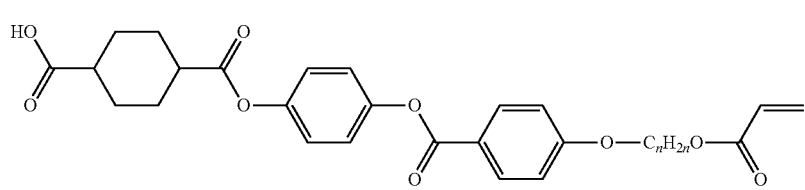
(R-42)
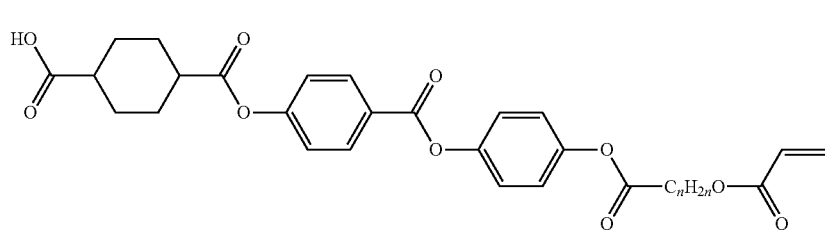
(R-43)
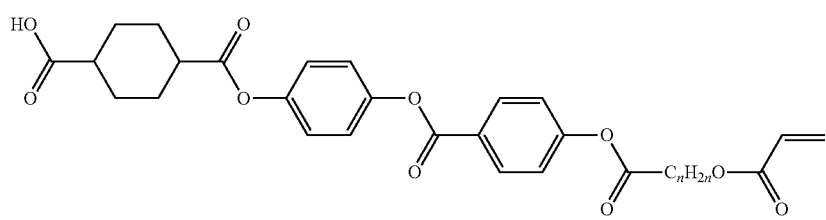
(R-44)
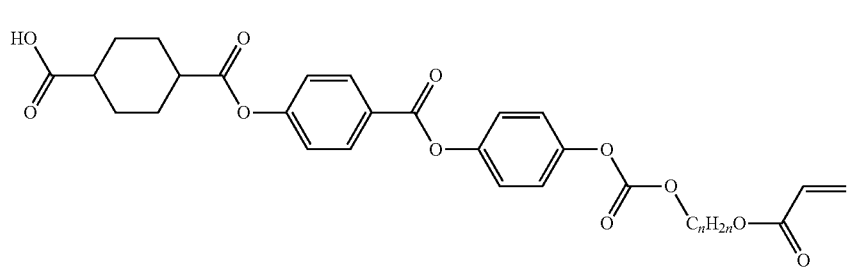
(R-45)
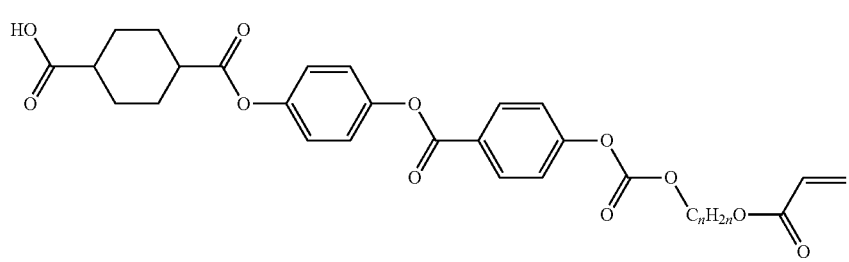
(R-46)

-continued
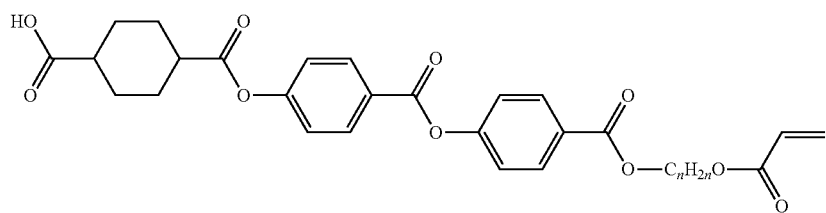
(R-47)
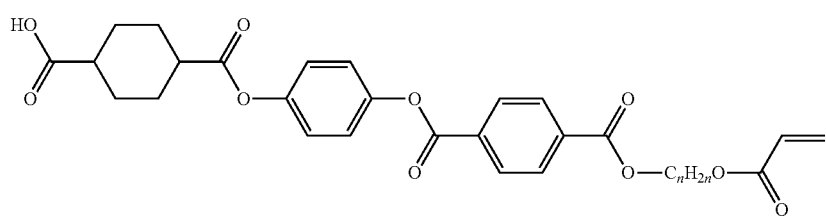
(R-48)
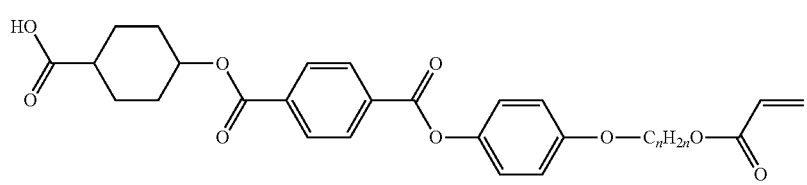
(R-49)
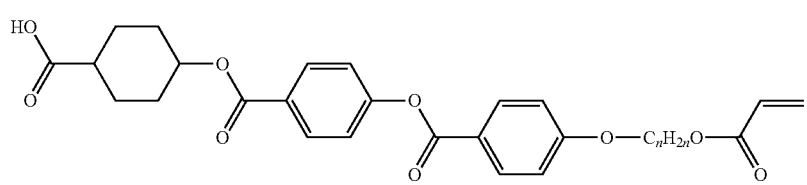
(R-50)
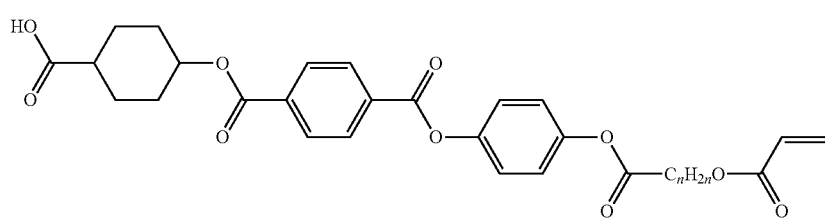
(R-51)
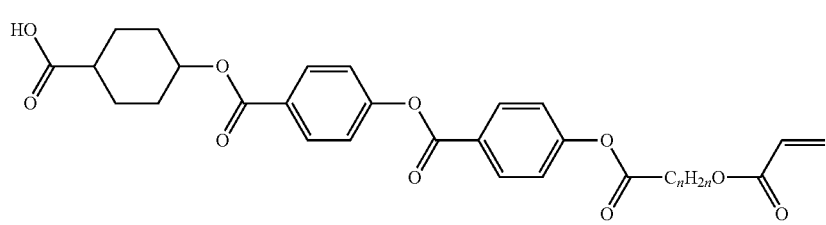
(R-52)
[Chemical Formula 18]
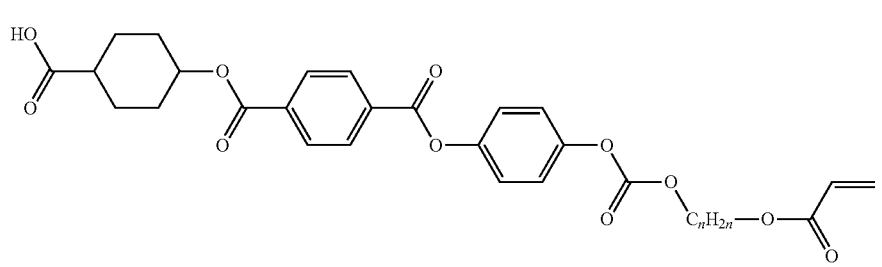
(R-53)

-continued
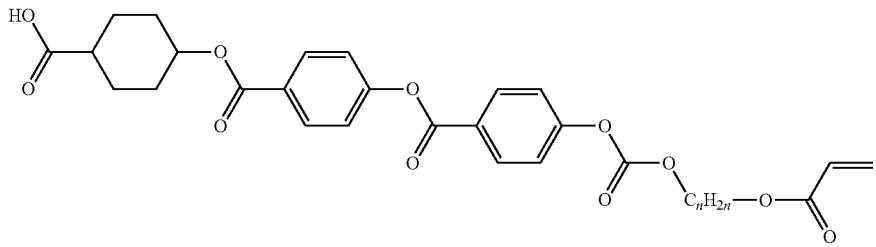
(R-54)
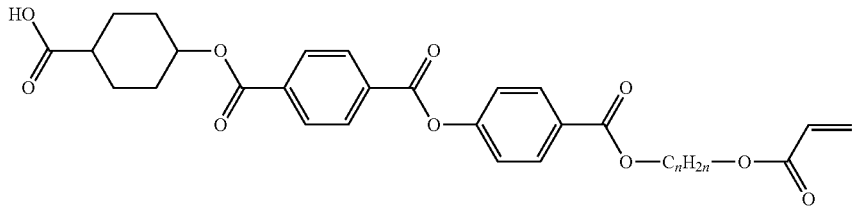
(R-55)
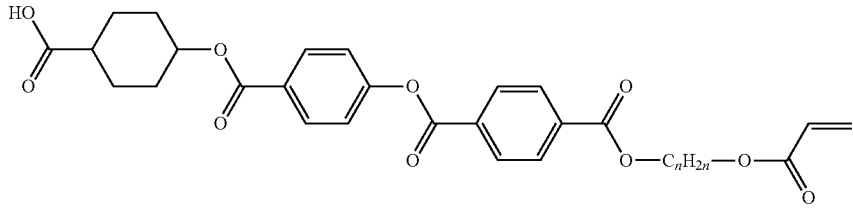
(R-56)
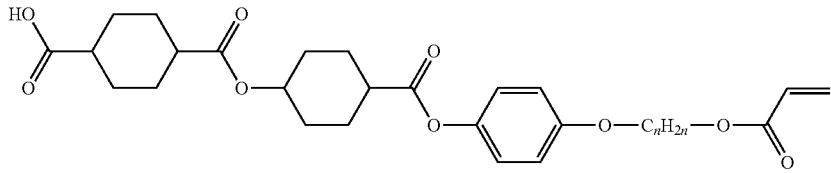
(R-57)
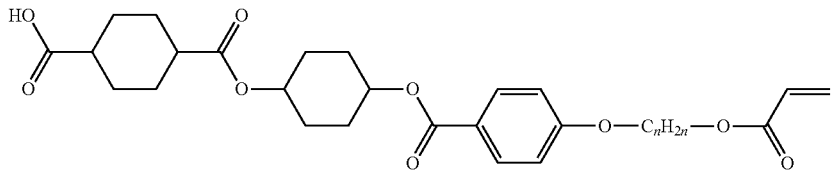
(R-58)
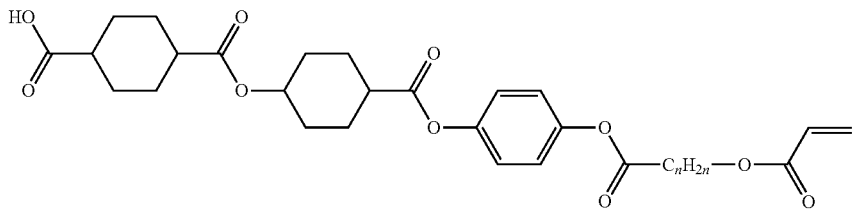
(R-59)
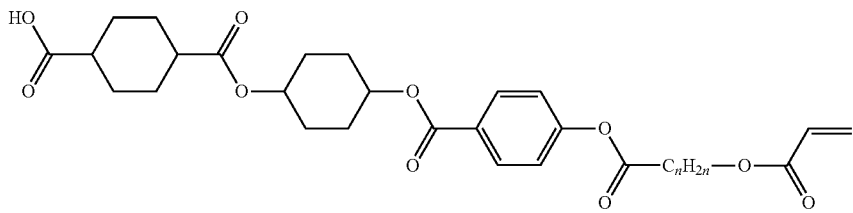
(R-60)

-continued
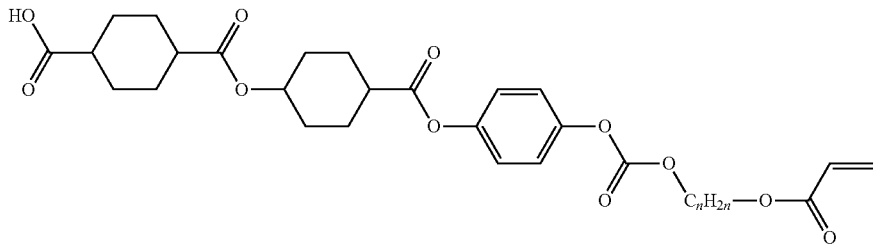
(R-61)
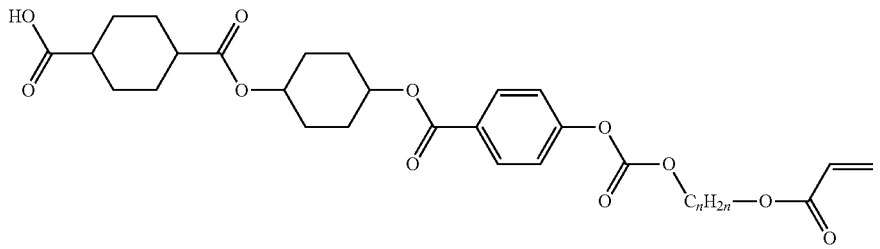
(R-62)
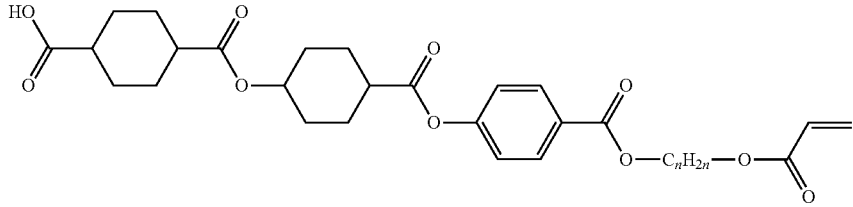
(R-63)
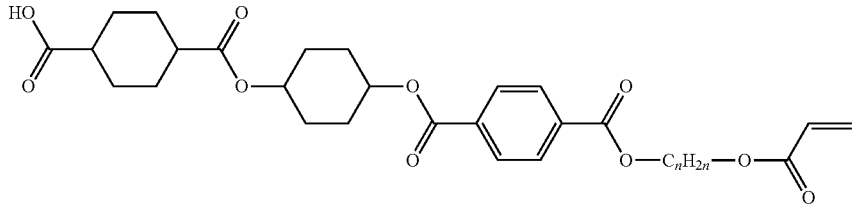
(R-64)
[Chemical Formula 19]
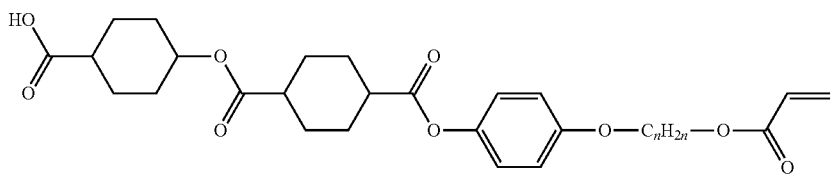
(R-65)
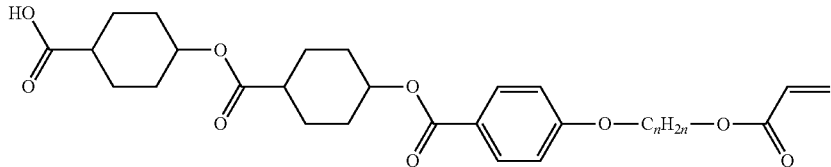
(R-66)
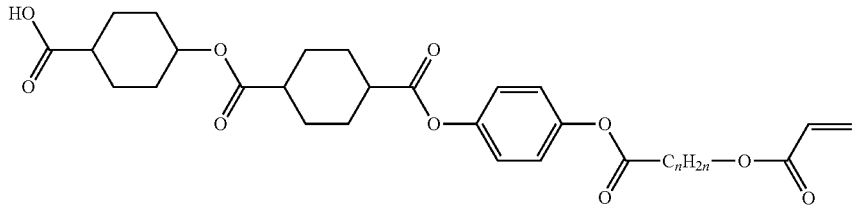
(R-67)

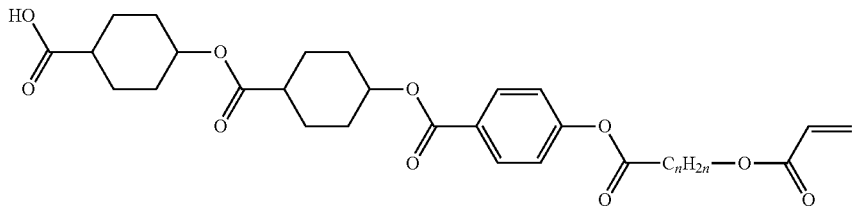
(R-68)
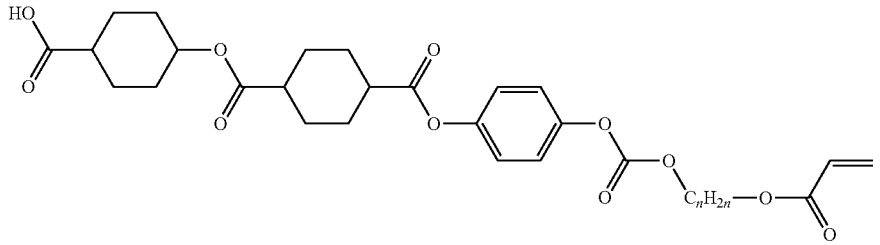
(R-69)
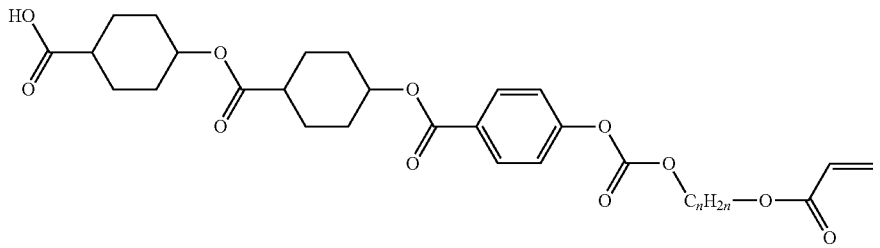
(R-70)
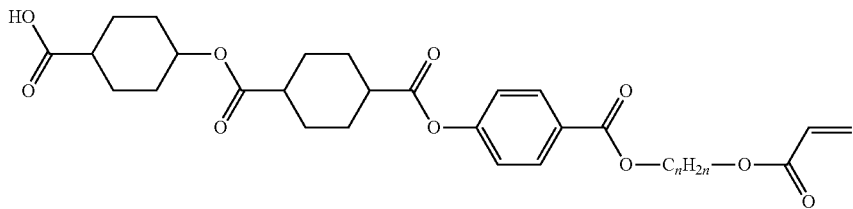
(R-71)
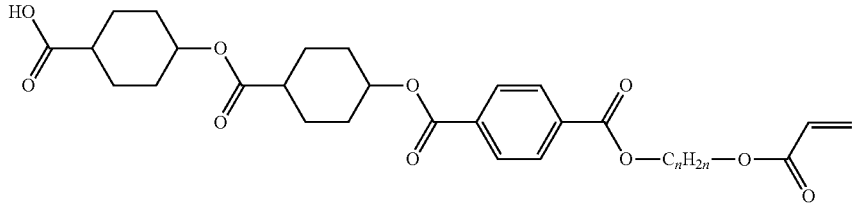
(R-72)
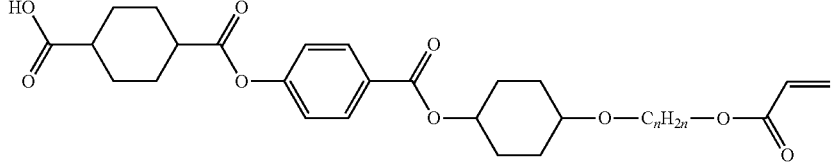
(R-73)
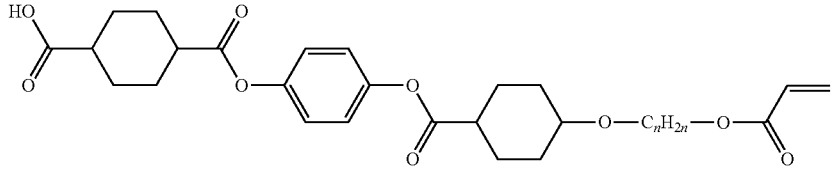
(R-74)

-continued
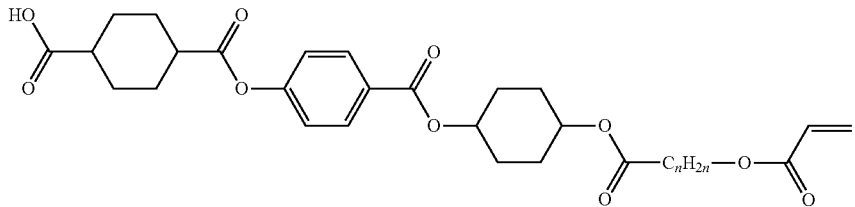
(R-75)
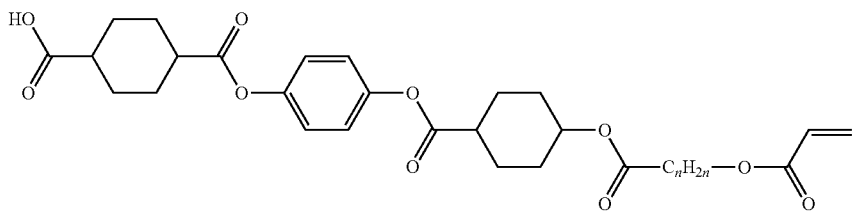
(R-76)
[Chemical Formula 20]
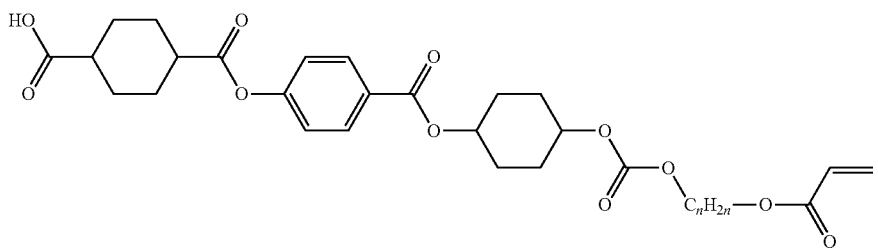
(R-77)
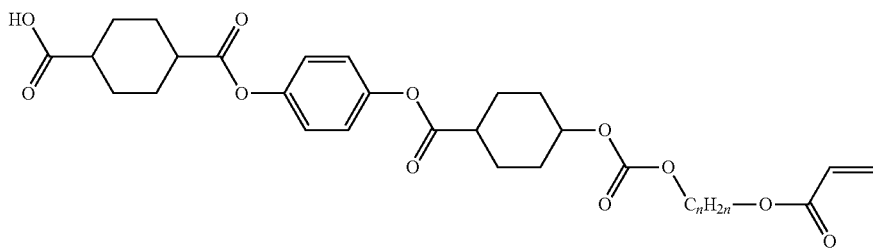
(R-78)
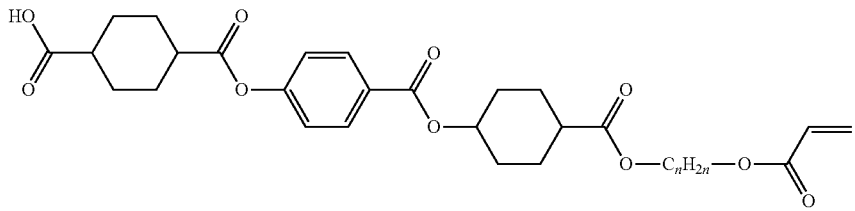
(R-79)
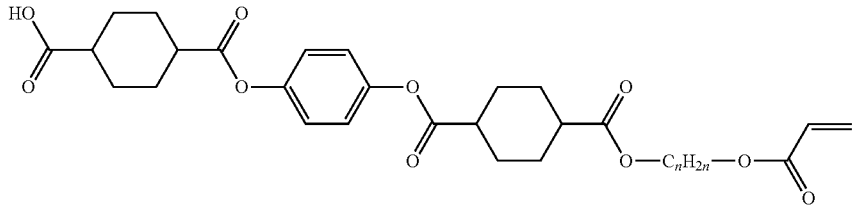
(R-80)
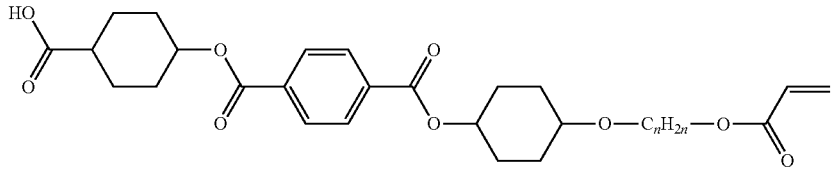
(R-81)

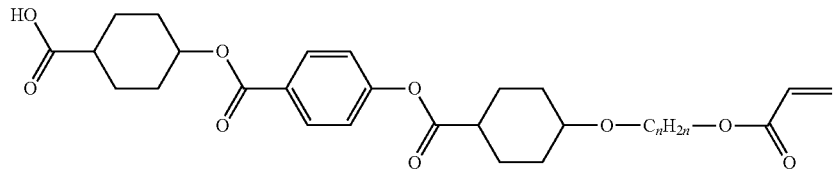
(R-82)
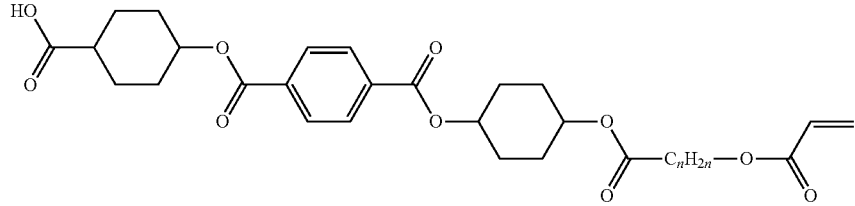
(R-83)
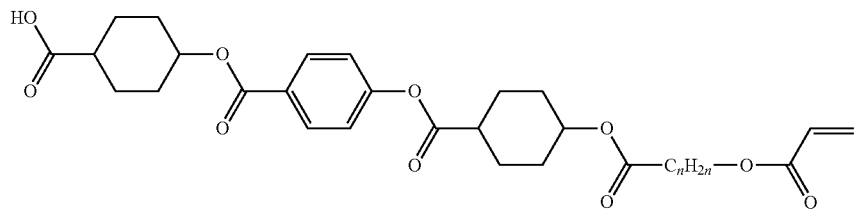
(R-84)
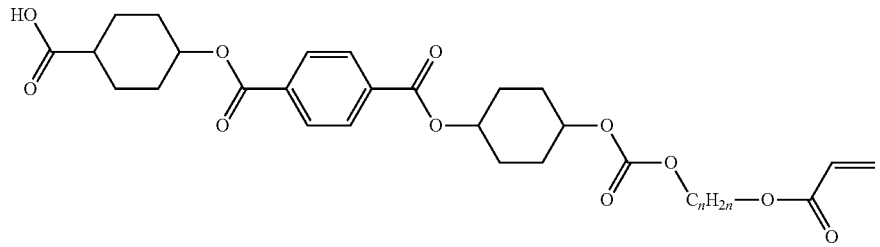
(R-85)
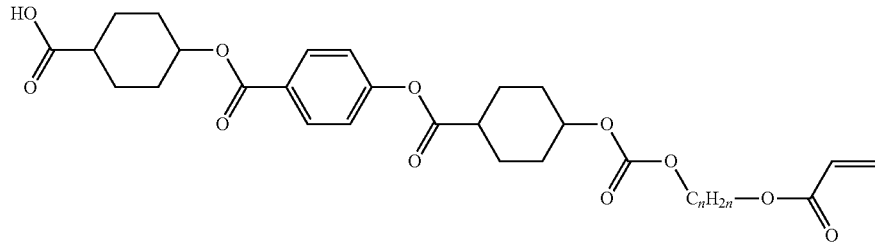
(R-86)
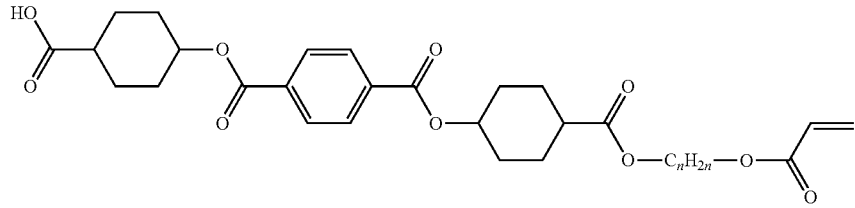
(R-87)
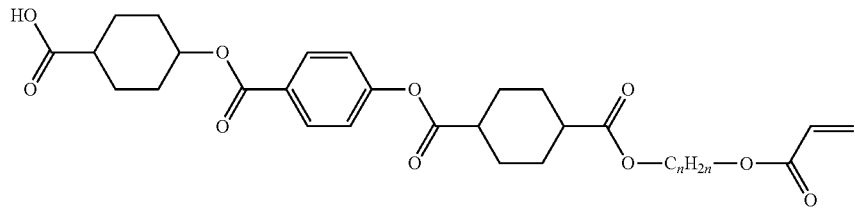
(R-88)

[Chemical Formula 21]
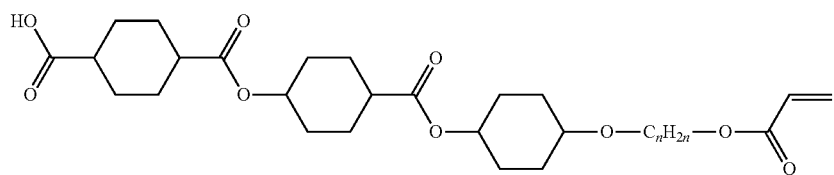 (R-89)
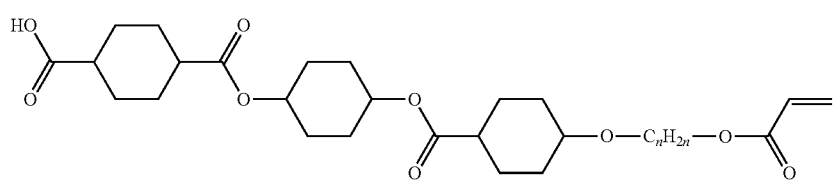 (R-90)
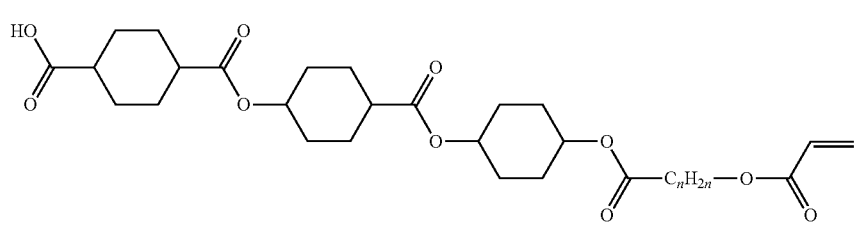 (R-91)
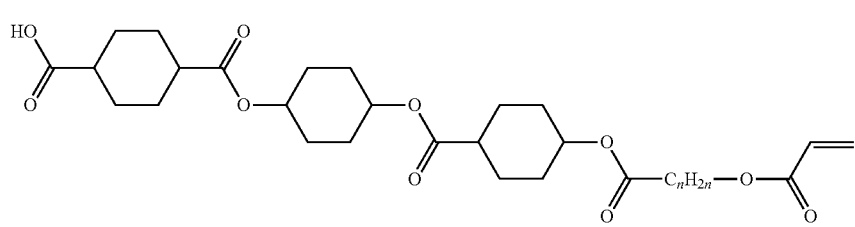 (R-92)
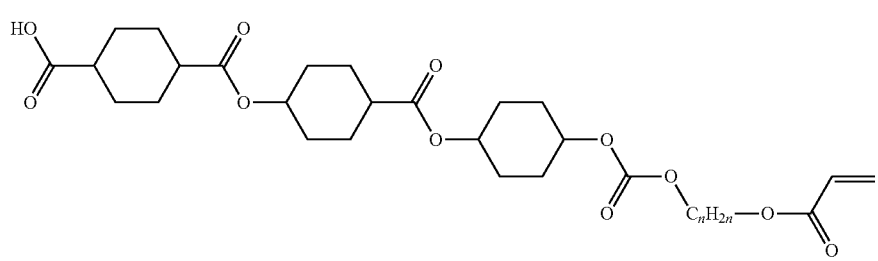 (R-93)
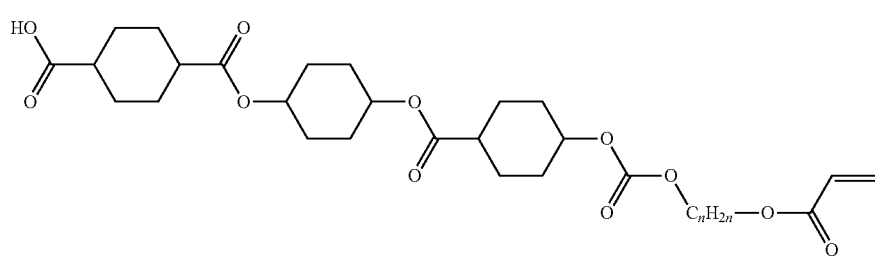 (R-94)
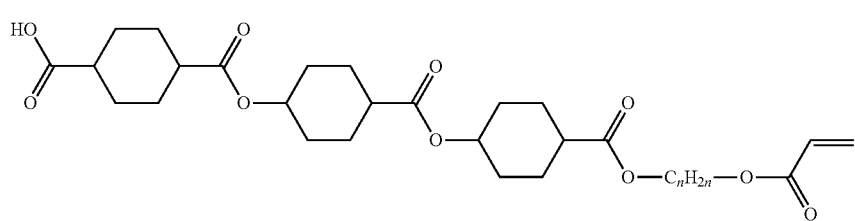 (R-95)

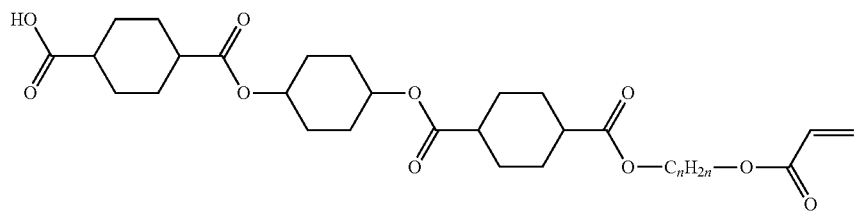
(R-96)
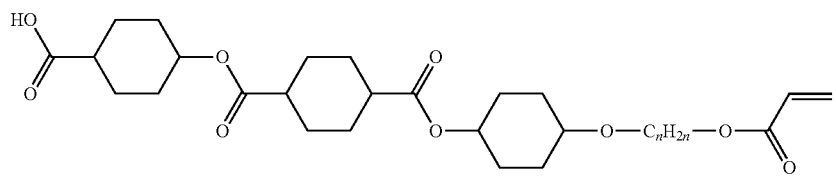
(R-97)
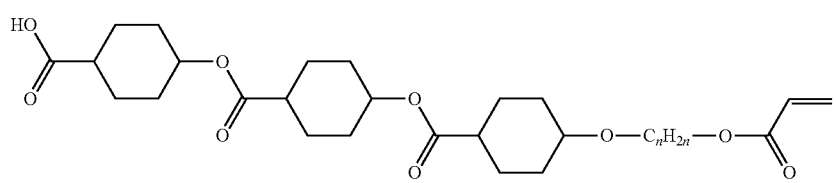
(R-98)
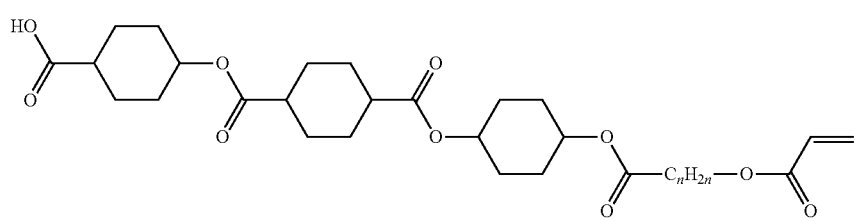
(R-99)
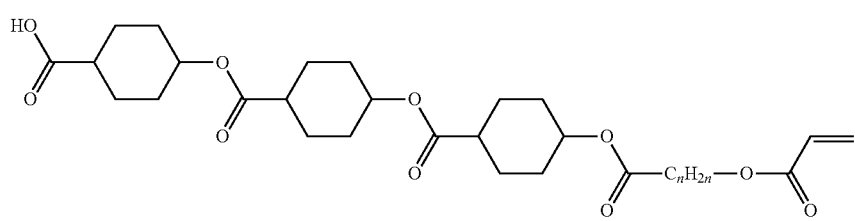
(R-100)
[Chemical Formula 22]
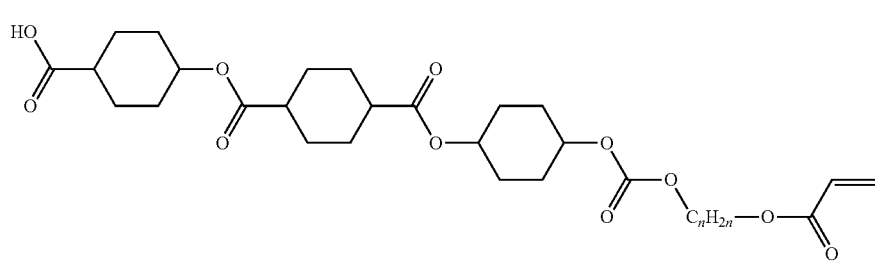
(R-101)
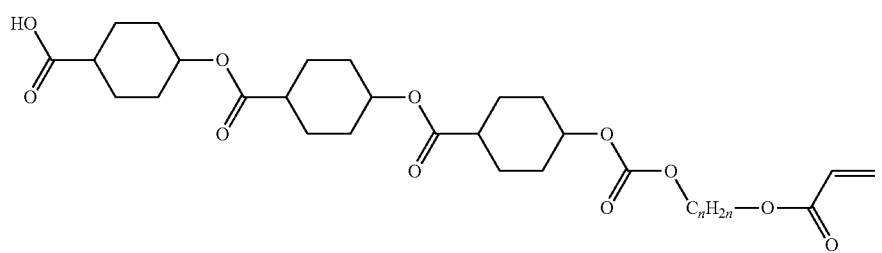
(R-102)

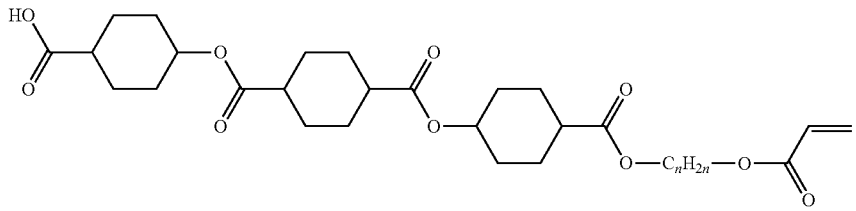
(R-103)

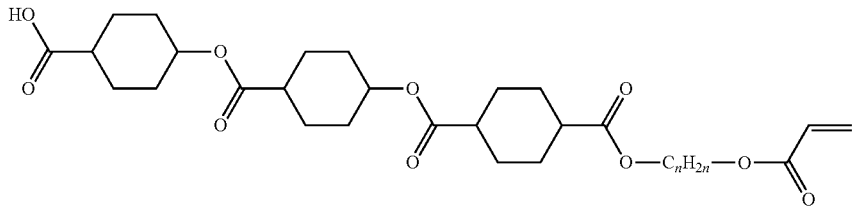
(R-104)

The esterification reaction of the alcohol compound (D-1) and the carboxylic acid compound (E-1) is preferably carried out in the presence of a condensing agent. By carrying out the esterification reaction in the presence of a condensing agent, the esterification reaction can be performed efficiently and quickly.

As the condensing agent, carbodiimide compounds such as 1-cyclohexyl-3-(2-morpholinoethyl)carbodiimide metho-p-toluenesulfonate, dicyclohexylcarbodiimide, diisopropylcarbodiimide, 1-ethyl-3-(3-dimethylaminopropyl)carbodiimide, 1-ethyl-3-(3-dimethylaminopropyl)carbodiimide hydrochloride (water soluble carbodiimide: commercially available as WSC), bis(2,6-diisopropylphenyl)carbodiimide and bis(trimethylsilyl)carbodiimide, 2-methyl-6-nitrobenzoic anhydride, 2,2'-carbonylbis-1H-imidazole, 1,1'-oxalyldiimidazole, diphenylphosphoryl azide, 1-(4-nitrobenzenesulfonyl)-1H-1,2,4-triazole, 1H-benzotriazol-1-yloxytripyrrolidinophosphonium hexafluorophosphate, 1H-benzotriazol-1-yloxytris(dimethylamino)phosphonium hexafluorophosphate, N,N,N',N'-tetramethyl-O—(N-succinimidyl)uronium tetrafluoroborate, N-(1,2,2,2-tetrachloroethoxycarbonyloxy)succinimide, N-carbobenzoxysuccinimide, O-(6-chlorobenzotriazol-1-yl)-N,N,N',N'-tetramethyluronium tetrafluoroborate, O-(6-chlorobenzotriazol-1-yl)-N,N,N',N'-tetramethyluronium hexafluorophosphate, 2-bromo-1-ethylpyridinium tetrafluoroborate, 2-chloro-1,3-dimethylimidazolinium chloride, 2-chloro-1,3-dimethylimidazolinium hexafluorophosphate, 2-chloro-1-methylpyridinium iodide, 2-chloro-1-methylpyridinium p-toluenesulfonate, 2-fluoro-1-methylpyridinium p-toluenesulfonate, pentachlorophenyl trichloroacetate, and the like.

The condensing agent is preferably a carbodiimide compound, 2,2'-carbonylbis-1H-imidazole, 1,1'-oxalyldiimidazole, diphenylphosphoryl azide, 1H-benzotriazol-1-yloxytripyrrolidinophosphonium hexafluorophosphate, 1H-benzotriazol-1-yloxytris(dimethylamino)phosphonium hexafluorophosphate, N,N,N',N'-tetramethyl-O—(N-succinimidyl)uronium tetrafluoroborate, N-(1,2,2,2-tetrachloroethoxycarbonyloxy)succinimide, O-(6-chlorobenzotriazol-1-yl)-N,N,N',N'-tetramethyluronium hexafluorophosphate, 2-chloro-1,3-dimethylimidazolinium chloride, 2-chloro-1,3-dimethylimidazolinium hexafluorophosphate, 2-chloro-1-methylpyridinium iodide, or 2-chloro-1-methylpyridinium p-toluenesulfonate.

The condensing agent is more preferably a carbodiimide compound, 2,2'-carbonylbis-1H-imidazole, 1H-benzotriazol-1-yloxytripyrrolidinophosphonium hexafluorophosphate, 1H-benzotriazol-1-yloxytris(dimethylamino)phosphonium hexafluorophosphate, N,N,N',N'-tetramethyl-O—(N-succinimidyl)uronium tetrafluoroborate, O-(6-chlorobenzotriazol-1-yl)-N,N,N',N'-tetramethyluronium hexafluorophosphate, 2-chloro-1,3-dimethylimidazolinium chloride or 2-chloro-1-methylpyridinium iodide, and further preferably a carbodiimide compound, from the viewpoint of economical efficiency.

Among carbodiimide compounds, the condensing agent is preferably dicyclohexylcarbodiimide, diisopropylcarbodiimide, 1-ethyl-3-(3-dimethylaminopropyl)carbodiimide, 1-ethyl-3-(3-dimethylaminopropyl)carbodiimide hydrochloride (water soluble carbodiimide: commercially available as WSC), or bis(2,6-diisopropylphenyl)carbodiimide.

The amount of the condensing agent to be used is preferably 2 to 4 mole, per 1 mole of the alcohol compound (D-1), from the viewpoint of easily obtaining the compound (A).

In the esterification reaction, N-hydroxysuccinimide, benzotriazole, p-nitrophenol, 3,5-dibutyl-4-hydroxytoluene and the like may be further added as additives, and mixed. The amount of the additive to be used is preferably 0.01 to 1.5 mole, per 1 mole of the alcohol compound (D-1), from the viewpoint of easily obtaining the compound (A).

The esterification reaction may be carried out in the presence of a catalyst. Examples of the catalyst include N,N-dimethylaminopyridine, N,N-dimethylaniline, dimethylammonium pentafluorobenzenesulfonate, and the like. Among them, N, N-dimethylaminopyridine and N, N-dimethylaniline are preferable, and N,N-dimethylaminopyridine is more preferable. The amount of the catalyst to be used is preferably 0.01 to 0.5 mole, per 1 mole of the alcohol compound (D-1), from the viewpoint of easily obtaining the compound (A).

The esterification reaction is usually carried out in a solvent. Examples of the solvent include ketone solvents such as acetone, methyl ethyl ketone, cyclopentanone, cyclohexanone, methyl amyl ketone and methyl isobutyl ketone; aliphatic hydrocarbon solvents such as pentane, hexane and heptane; aromatic hydrocarbon solvents such as toluene, xylene, benzene and chlorobenzene; nitrile solvents such as acetonitrile; ether solvents such as tetrahydrofuran and dimethoxyethane; ester solvents such as ethyl lactate; halogenated hydrocarbon solvents such as chloroform and dichloromethane; aprotic polar solvents such as dimethyl sulfoxide, N-methyl-2-pyrrolidone, N,N-dimethylformamide, N,N-dimethylacetamide and hexamethylphosphoric triamide; and the like. These organic solvents may be used alone or in combination.

The solvent is preferably a nonpolar organic solvent such as pentane, hexane, heptane, toluene, xylene, benzene, chlorobenzene, chloroform or dichloromethane, more preferably toluene, xylene, benzene, chlorobenzene, chloroform or dichloromethane, from the viewpoint of reaction yield and productivity. These organic solvents may be used alone or in combination.

The amount of the carboxylic acid compound (E-1) to be used is preferably 0.1 to 1.2 mole, more preferably 0.5 to 1.2 mole, and further preferably 0.5 to 1.0 mole, per 1 mole of the alcohol compound (D-1), from the viewpoint of easily obtaining the compound (A).

The amount of the solvent to be used is preferably 0.5 to 50 parts by mass, more preferably 1 to 20 parts by mass, and further preferably 2 to 10 parts by mass, based on 1 part by mass of the total of the alcohol compound (D-1) and the carboxylic acid compound (E-1).

The temperature of the esterification reaction is preferably from −20 to 120° C., more preferably from −20 to 60° C., and further preferably from −10 to 20° C., from the viewpoint of reaction yield and productivity. Also, the esterification reaction time is preferably 1 minute to 72 hours, more preferably 1 to 48 hours, and further preferably 1 to 24 hours, from the viewpoint of reaction yield and productivity. A compound (A) can be obtained from the obtained suspension by a method such as filtration or decantation.

In a case of $P^2=P^3$, $F^2=F^3$, $B^2=B^3$, $A^2=A^3$, $m^2=m^3$, $E^2=E^3$, $G^2=G^3$, $n^2=n^3$, and $D^2=D^3$, the polymerizable liquid crystal compound represented by the formula (B) can be produced, for example, by carrying out an esterification reaction of an alcohol compound (D-2) represented by formula (D-2):

[Chemical Formula 23]

(D-2)

with a carboxylic acid compound (E-2) represented by formula (E-2):

[Chemical Formula 24]

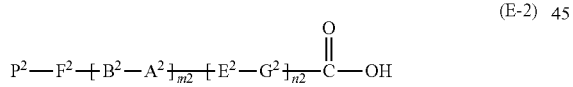

(E-2)

$Ar^2$, $P^2$, $F^2$, $B^2$, $A^2$, $m^2$, $E^2$, $G^2$ and $n^2$ in the formulas (D-2) and (E-2) have the same meanings as the symbols in the formula (B), and the preferred description applies equally. Examples of the carboxylic acid compound (E-2) include the above-mentioned compounds for the carboxylic acid compound (E-1).

The esterification reaction of the alcohol compound (D-2) and the carboxylic acid compound (E-2) is preferably carried out in the presence of a condensing agent from the viewpoint of efficiently and rapidly carrying out the esterification reaction. The description regarding the condensing agent stated above for the esterification reaction of the alcohol compound (D-1) and the carboxylic acid compound (E-1) equally applies to the esterification reaction of the alcohol compound (D-2) and the carboxylic acid compound (E-2), unless otherwise specified.

The amount of the condensing agent to be used is preferably 2 to 4 mole, per 1 mole of the alcohol compound (D-2), from the viewpoint of easily obtaining the polymerizable liquid crystal compound (B).

The esterification reaction of the alcohol compound (D-2) and the carboxylic acid compound (E-2) may be carried out in the presence of a catalyst. As to the catalyst, the description concerning the catalyst in the esterification reaction of the alcohol compound (D-1) and the carboxylic acid compound (E-1) applies equally. The amount of the catalyst to be used is preferably 0.01 to 0.5 mole, per 1 mole of the alcohol compound (D-2), from the viewpoint of easily obtaining the polymerizable liquid crystal compound (B).

The esterification reaction of the alcohol compound (D-2) and the carboxylic acid compound (E-2) is usually carried out in a solvent. As to the solvent, the description concerning the solvent in the esterification reaction of the alcohol compound (D-1) and the carboxylic acid compound (E-1) applies equally.

The amount of the carboxylic acid compound (E-2) to be used is preferably 2 to 10 mole, more preferably 2 to 5 mole, and further preferably 2 to 3 mole, per 1 mole of the alcohol compound (D-2), from the viewpoint of easily obtaining the polymerizable liquid crystal compound (B).

The amount of the solvent to be used is preferably 0.5 to 50 parts by mass, more preferably 1 to 20 parts by mass, and further preferably 2 to 10 parts by mass, based on 1 part by mass of the total of the alcohol compound (D-2) and the carboxylic acid compound (E-2).

As to the temperature and time of the esterification reaction, the description in the esterification reaction of the alcohol compound (D-1) and the carboxylic acid compound (E-1) applies equally.

The present invention also provides a liquid crystal composition containing at least one compound (A) represented by the formula (A) and at least one polymerizable liquid crystal compound (B) represented by the formula (B). From the viewpoint of easily enhancing compatibility between the compound (A) and the polymerizable liquid crystal compound (B) and easily preparing each compound, it is preferable that, in the formula (A) and the formula (B), $B^1$ and $B^2$ and $B^3$ are the same, $E^1$ and $E^2$ and $E^3$ are the same, $D^2$ and $D^2$ and $D^3$ are the same, $A^1$ and $A^2$ and $A^3$ are the same, $G^1$ and $G^2$ and $G^3$ are the same, $F^1$ and $F^2$ and $F^3$ are the same, m1 and m2 and m3 are the same, n1 and n2 and n3 are the same, $Ar^1$ and $Ar^2$ are the same, and $P^1$ and $P^2$ and $P^3$ are the same.

In the liquid crystal composition of the present invention, the area percentage value of the compound represented by the formula (A) as measured by liquid chromatography is 18% or less based on the sum of area values of the compound (A) and the polymerizable liquid crystal compound (B) contained in the liquid crystal composition. When the area percentage value of the compound (A) exceeds 18%, the compound (A) precipitates as crystals or prevents the alignment of the polymerizable liquid crystal compound (B), thus alignment defects are generated and desired optical characteristics may not to be obtained in some cases. Here, the area percentage value of the compound (A) contained in the liquid crystal composition corresponds to the content (% by mass) of the compound (A) contained in the liquid crystal composition, and is calculated from the area value of the compound (A) and the area value of the polymerizable liquid crystal compound (B) contained in the liquid crystal composition measured by HPLC according to following formula (II). The details of the HPLC measurement conditions are as shown in examples.

[Expression 1]

$$\text{Area Percentage of Compound }(A) = \frac{\text{Area Value of Compound }(A)}{\text{Area Value of Compound }(A) + \text{Area Value of Polymerizable Liquid Crystal Compound }(B)} \times 100 \quad \text{(II)}$$

The area percentage value of the compound (A) is preferably 0.05% or more, more preferably 0.07% or more, and still more preferably 0.10% or more, based on the sum of area values of the compound (A) and the polymerizable liquid crystal compound (B) contained in the liquid crystal composition. Also, the area percentage value of the compound (A) is preferably 18% or less, more preferably 15% or less, and still more preferably 10% or less, based on the sum of area values of the compound (A) and the polymerizable liquid crystal compound (B) contained in the liquid crystal composition. When the area percentage value of the compound (A) is not less than the above lower limit, the nematic phase transition temperature is easily lowered, and the polymerizable liquid crystal compound is hard to precipitate during storage of the liquid crystal composition of the present invention. When the area percentage value of the compound (A) is not more than the above upper limit, the alignment state of the liquid crystal can be kept in good condition when producing the film, thus alignment defect is hard to occur.

The maximum absorption wavelength ($\lambda_{max}$) of the liquid crystal composition of the present invention is preferably 300 to 400 nm, more preferably 315 to 385 nm, and further preferably 320 to 380 nm. When the maximum absorption wavelength ($\lambda_{max}$) of the liquid crystal composition is not less than the lower limit described above, the retardation film composed of the polymer in the alignment state of the liquid crystal composition tends to easily exhibit reverse wavelength dispersibility. When the maximum absorption wavelength ($\lambda_{max}$) of the liquid crystal composition is not more than the above upper limit, absorption in the visible light region is suppressed, thus coloring of the film can be suppressed.

The liquid crystal composition of the present invention may contain an organic solvent as it facilitates handling and film formation when forming an optical film such as a retardation film.

The organic solvent which can be contained in the liquid crystal composition of the present invention is an organic solvent capable of dissolving the compound (A), the polymerizable liquid crystal compound (B) and the like, and is not particularly limited as long as it is a solvent inert to the polymerization reaction. Examples of the organic solvent include alcohols such as methanol, ethanol, ethylene glycol, isopropyl alcohol, propylene glycol, methyl cellosolve, butyl cellosolve and propylene glycol monomethyl ether; ester solvents such as ethyl acetate, butyl acetate, ethylene glycol methyl ether acetate, γ-butyrolactone, propylene glycol methyl ether acetate and ethyl lactate; ketone solvents such as acetone, methyl ethyl ketone, cyclopentanone, cyclohexanone, methyl amyl ketone and methyl isobutyl ketone; non-chlorinated aliphatic hydrocarbon solvents such as pentane, hexane and heptane; non-chlorinated aromatic hydrocarbon solvents such as toluene, xylene and phenol; nitrile solvents such as acetonitrile; ether solvents such as tetrahydrofuran and dimethoxyethane; chlorinated solvents such as chloroform and chlorobenzene; amide solvents such as N-methylpyrrolidone (NMP) and N, N-dimethylformamide (DMF); and the like. From the viewpoint of easily dissolving the compound (A) and the polymerizable liquid crystal compound (B), an ester solvent, a ketone solvent, a non-chlorinated aromatic hydrocarbon solvent, an ether solvent and an amide solvent are preferable, and a ketone solvent and an amide solvent are more preferable, and an amide solvent is still more preferable. These organic solvents may be used alone or in combination.

The content of the organic solvent in the liquid crystal composition of the present invention is preferably 100 to 10000 parts by mass, more preferably 200 to 5000 parts by mass, and further preferably 500 to 2500 parts by mass, based on 100 parts by mass of the polymerizable liquid crystal compound (B).

In addition, the liquid crystal composition of the present invention is excellent in solubility in an organic solvent by containing the compound (A) and the polymerizable liquid crystal compound (B). Therefore, the liquid crystal composition of the present invention is advantageous in that it is excellent in stability during storage and can reduce the amount of the organic solvent used during coating, storage and the like. For example, in the case of using N-methylpyrrolidone as a solvent, even when the content of the solvent is, for example, 2,500 parts by mass or less based on 100 parts by mass of the polymerizable liquid crystal compound (B), precipitation of the polymerizable liquid crystal compound (B) can be suppressed over a long period (for example, 24 hours or more, and preferably 72 hours or more).

The liquid crystal composition of the present invention can be obtained, for example, by mixing the compound (A) and the polymerizable liquid crystal compound (B), previously separately prepared by the method described above as the method for producing the compound (A) and the polymerizable liquid crystal compound (B), in such a manner that the area percentage value of the compound (A) is a predetermined value. Also, the amount may be further adjusted to a predetermined range by using a mixture of the compound (A) and the polymerizable liquid crystal compound (B) obtained in the production method of the compound (A).

The present invention also provides a layer containing a cured product of the above-mentioned liquid crystal composition of the present invention. The layer containing a cured product of the liquid crystal composition of the present invention can be produced, for example, by coating the liquid crystal composition of the present invention on a supporting substrate, optionally through an alignment film, aligning the polymerizable liquid crystal compound contained in the liquid crystal composition, then polymerizing the polymerizable liquid crystal compound by photopolymerization or the like, and curing the obtained compound. In the method for producing a layer of the present invention, the method described later is applied equally in detail, for example, as a method for producing a retardation film containing the layer.

The layer containing a cured product of the liquid crystal composition of the present invention can be used alone, or in the form of a laminate with a support or the like, as an optical film such as a retardation film or a polarizing film. The present invention also provides an optical film having at least the layer, a retardation film having at least the layer, and a retardation film having reverse wavelength dispersibility having at least the layer.

For example, in one embodiment of the present invention, a retardation film (hereinafter, also referred to as "the retardation film of the present invention") composed of a polymer (cured product) in an alignment state of the liquid crystal composition is provided. The retardation film of the present invention preferably satisfies the wavelength dispersibility Re(450 nm)/Re(550 nm) of the following formula (I).

$$0.80 \leq Re(450)/Re(550) < 1.00 \qquad (I)$$

wherein Re(λ) represents a front retardation value for light at a wavelength of λ nm.

The wavelength dispersibility Re(450 nm)/Re(550 nm) of the retardation film of the present invention is more preferably 0.8 or more and less than 0.98, and further preferably 0.8 or more and less than 0.96. When the wavelength dispersibility Re(450 nm)/Re(550 nm) of the retardation film of the present invention is not less than the above lower limit, circular polarization conversion becomes possible in the short wavelength region around 450 nm, thus it is preferable. When the wavelength dispersibility Re(450 nm)/Re(550 nm) of the retardation film of the present invention is less than the above upper limit value, the obtained retardation film exhibits reverse wavelength dispersibility, thus it is preferable.

The retardation film of the present invention is excellent in transparency and can be used in various optical displays. The thickness of the retardation film is preferably from 0.1 to 10 μm, and further preferably from 0.5 to 3 μm from the viewpoint of reducing photoelasticity.

When the retardation film of the present invention is used for a λ/4 plate, the retardation value (Re(550 nm)) at a wavelength of 550 nm of the obtained retardation film is preferably 113 to 163 nm, more preferably 130 to 150 nm, and particularly preferably about 135 nm to 150 nm.

In order to use the retardation film of the present invention as an optical film for VA (Vertical Alignment) mode, the film thickness of the retardation film may be adjusted so that Re(550 nm) is set to preferably about 40 to 100 nm, and more preferably about 60 to 80 nm.

By combining the retardation film of the present invention with a polarizing film, a polarizing plate (hereinafter, also referred to as "the polarizing plate of the present invention"), particularly, an elliptically polarizing plate and a circularly polarizing plate are provided. In the elliptically polarizing plate and the circularly polarizing plate, the retardation film of the present invention is laminated on the polarizing film. Also, in the present invention, a broadband circularly polarizing plate obtained by further laminating the retardation film of the present invention as a broadband λ/4 plate on the elliptically polarizing plate or circularly polarizing plate can be also provided.

In one embodiment of the present invention, it can be used for optical displays including the polarizing plate of the present invention, for example, reflective liquid crystal displays and organic electroluminescence (EL) displays. The FPD is not particularly limited, and examples thereof include a liquid crystal display (LCD) device and an organic EL display device.

In the present invention, the optical display includes the polarizing plate of the present invention, and examples thereof include a liquid crystal display device including a laminate in which the polarizing plate of the present invention and a liquid crystal panel are laminated, and an organic EL display device including an organic EL panel in which the polarizing plate of the present invention and a light emitting layer are laminated.

In the present invention, the retardation film is a film used for converting linearly polarized light into circularly polarized light or elliptically polarized light, and converting circularly polarized light or elliptically polarized light into linearly polarized light. The retardation film of the present invention contains a polymer (cured product) of the liquid crystal composition of the present invention.

The retardation film of the present invention can be produced, for example, by the following method.

First, an additive such as the following polymerization initiator, polymerization inhibitor, photosensitizer or leveling agent may be added to the liquid crystal composition containing the compound (A) of the present invention and the polymerizable liquid crystal compound (B), and the organic solvent as necessary, to prepare a mixed solution. In particular, it is preferable to contain the organic solvent as it facilitates film formation when forming a film, and it is preferable to contain a polymerization initiator as it has a function of curing the obtained retardation film.

The viscosity of the mixed solution containing the liquid crystal composition of the present invention is preferably adjusted to, for example, 10 mPa·s or less, and preferably about 0.1 to 7 mPa·s, so as to easily apply the mixed solution. The viscosity of the mixed solution can be adjusted according to the content of the organic solvent.

Further, the concentration of the solid content in the mixed solution is, for example, 5 to 50% by mass, preferably 5 to 30%, and more preferably 5% to 15%. The term "solid content" as used herein refers to a component obtained by removing a solvent from the mixed solution (liquid crystal composition). When the concentration of the solid content is 5% or more, the retardation film does not become too thin, and there is a tendency that a birefringence index necessary for optical compensation of the liquid crystal panel is given. Moreover, when the concentration of the solid content is 50% or less, the viscosity of the mixed solution is low, thus unevenness in the film thickness of the retardation film tends to hardly occur, which is preferable.

Examples of the polymerization initiator include a photopolymerization initiator and a thermal polymerization initiator, and it is preferably a photopolymerization initiator.

Examples of the photopolymerization initiator include benzoins, benzophenones, benzil ketals, α-hydroxy ketones, α-aminoketones, iodonium salts, sulfonium salts and the like, and more specifically, Irgacure 907, Irgacure 184, Irgacure 651, Irgacure 819, Irgacure 250, Irgacure 369 (all manufactured by Ciba Japan Co., Ltd.), SEIKUOL BZ, SEIKUOL Z, SEIKUOL BEE (all manufactured by Seiko Chemical Co., Ltd.), Kayacure BP100 (manufactured by Nippon Kayaku Co., Ltd.), Kayacure UVI-6992 (manufactured by The Dow Chemical Company), ADEKA OPTOMER SP-152 or ADEKA OPTOMER SP-170 (all manufactured by ADEKA CORPORATION), and the like.

The content of the polymerization initiator is, for example, 0.1 to 30 parts by mass, preferably 0.5 to 20 parts by mass, and more preferably 0.5 to 10 parts by mass, based on 100 parts by mass of the polymerizable liquid crystal compound (B). Within the above range, the polymerizable liquid crystal compound (B) can be polymerized without disturbing alignment of the liquid crystal compound.

Examples of the polymerization inhibitor include hydroquinones, hydroquinones having a substituent such as alkyl ethers, catechols having substituents such as alkyl ethers such as butyl catechol, pyrogallols, radical scavengers such as 2,2,6,6-tetramethyl-1-piperidinyloxy radicals, thiophenols, β-naphthylamines or β-naphthols, and the like.

By using the polymerization inhibitor, the polymerization of the polymerizable liquid crystal compound (B) can be controlled, and the stability of the obtained retardation film can be improved. The amount of the polymerization inhibitor to be used is, for example, 0.05 to 30 parts by mass, and preferably 0.1 to 10 parts by mass, based on 100 parts by mass of the polymerizable liquid crystal compound (B). Within the above range, the polymerizable liquid crystal compound (B) can be polymerized without disturbing alignment of the liquid crystal compound.

Examples of the photosensitizer include xanthones such as xanthone and thioxanthone, anthracenes, anthracenes having a substituent such as alkyl ethers, phenothiazine or rubrene.

By using a photosensitizer, the polymerization of the polymerizable liquid crystal compound (B) can be highly sensitized. The amount of the photosensitizer to be used is, for example, 0.05 to 30 parts by mass, and preferably 0.1 to 10 parts by mass, based on 100 parts by mass of the polymerizable liquid crystal compound (B). Within the above range, the polymerizable liquid crystal compound (B) can be polymerized without disturbing alignment of the liquid crystal compound.

Examples of the leveling agent include additives for radiation curable coating (BYK-352, BYK-353, BYK-361N, manufactured by BYK Japan KK), coating additives (SH28PA, DC11PA, ST80PA, manufactured by Dow Corning Toray Co., Ltd.), coating additives (KP321, KP323, X22-161A, KF6001, manufactured by Shin-Etsu Chemical Co., Ltd.), fluorine-based additives (F-445, F-470, F-479, manufactured by DIC CORPORATION), and the like.

By using the leveling agent, the obtained retardation film can be smoothed. Further, in the process of producing the retardation film, it is possible to control the fluidity of the mixed solution containing the liquid crystal composition, or to adjust the crosslinking density of the retardation film obtained by polymerizing the polymerizable liquid crystal compound (B). The specific numerical value of the amount of the leveling agent to be used is, for example, 0.05 to 30 parts by mass, and preferably 0.05 to 10 parts by mass, based on 100 parts by mass of the polymerizable liquid crystal compound (B). Within the above range, the polymerizable liquid crystal compound (B) can be polymerized without disturbing alignment of the liquid crystal compound.

Subsequently, a mixed solution containing the liquid crystal composition of the present invention is coated on a supporting substrate and dried, thereby obtaining an unpolymerized film. When the unpolymerized film shows a liquid crystal phase such as a nematic phase, the obtained retardation film has birefringence by monodomain alignment. Since the unpolymerized film is aligned at a low temperature of about 0 to 120° C., and preferably 25 to 80° C., it is possible to use a supporting substrate which is not necessarily sufficient in terms of heat resistance as an alignment film. Also, crystallization does not occur even when the unpolymerized film is further cooled to about 30 to 10° C. after alignment, thus handling is easy.

By properly adjusting the coating amount and concentration of the mixed solution, it is possible to adjust the film thickness so as to give desired retardation. In the case of a mixed solution in which the amounts of the compound (A) of the present invention and the polymerizable liquid crystal compound (B) are constant, the retardation value (retardation value, $Re(\lambda)$) of the obtained retardation film is determined as formula (III), thus the film thickness d may be adjusted in order to obtain the desired $Re(\lambda)$.

$$Re(\lambda)=d\times\Delta n(\lambda) \quad \text{(III)}$$

wherein $Re(\lambda)$ represents a retardation value at a wavelength of $\lambda$ nm, d represents a film thickness, and $\Delta n(\lambda)$ represents a birefringence index at a wavelength $\lambda$ nm.

Examples of a method for coating a supporting substrate include an extrusion coating method, a direct gravure coating method, a reverse gravure coating method, a CAP coating method, a die coating method, and the like. Also, examples thereof include methods for coating a supporting substrate with a coater such as a dip coater, a bar coater or a spin coater.

Examples of the supporting substrate include glass, a plastic sheet, a plastic film and a translucent film. Examples of the translucent film include polyolefin films such as polyethylene, polypropylene and norbornene polymers, polyvinyl alcohol films, polyethylene terephthalate films, polymethacrylic acid ester films, polyacrylic acid ester films, cellulose ester films, polyethylene naphthalate films, polycarbonate films, polysulfone films, polyethersulfone films, polyetherketone films, polyphenylene sulfide films, polyphenylene oxide films, and the like.

For example, even in processes requiring the strength of the retardation film, such as a lamination process, a transportation process and a storage process of the retardation film of the present invention, it can be easily handled without breakage or the like by using the supporting substrate.

In addition, it is preferable to form an alignment film on a supporting substrate and coat a mixed solution containing the liquid crystal composition of the present invention on the alignment film. It is preferable that the alignment film has solvent resistance not to be dissolved in the mixed solution when coating the mixed solution containing the liquid crystal composition of the present invention and the like, has heat resistance during heat treatment for removal of the solvent and alignment of the liquid crystal, and does not occur peeling due to friction or the like during rubbing, and it is preferable that the alignment film is composed of a polymer or a composition containing a polymer.

Examples of the polymer include polymers such as polyamide and gelatin having an amide bond in the molecule, polyimide having an imide bond in the molecule and polyamic acid which is a hydrolyzate thereof, polyvinyl alcohols, alkyl-modified polyvinyl alcohols, polyacrylamide, polyoxazole, polyethyleneimine, polystyrene, polyvinylpyrrolidone, polyacrylic acid, and polyacrylic acid esters. These polymers may be used alone, or two or more of them may be mixed or copolymerized. These polymers can be easily obtained by polycondensation by dehydration, deamination or the like, chain polymerization such as radical polymerization, anion polymerization or cationic polymerization, coordination polymerization, ring opening polymerization or the like.

Also, these polymers can be dissolved in a solvent and applied. Specific examples of the solvent include, but are not limited to, water; alcohols such as methanol, ethanol, ethylene glycol, isopropyl alcohol, propylene glycol, methyl cellosolve, butyl cellosolve and propylene glycol monomethyl ether; ester solvents such as ethyl acetate, butyl acetate, ethylene glycol methyl ether acetate, γ-butyrolactone, propylene glycol methyl ether acetate and ethyl lactate; ketone solvents such as acetone, methyl ethyl ketone, cyclopentanone, cyclohexanone, methyl amyl ketone and methyl isobutyl ketone; non-chlorinated aliphatic hydrocarbon solvents such as pentane, hexane and heptane; non-chlorinated aromatic hydrocarbon solvents such as toluene and xylene; nitrile solvents such as acetonitrile; ether solvents such as tetrahydrofuran and dimethoxyethane; chlorinated solvents such as chloroform and chlorobenzene; and the like. These organic solvents may be used alone or in combination.

In order to form an alignment film, a commercially available alignment film material may be used as it is. Examples of the commercially available alignment film material include SUNEVER (registered trademark, manufactured by Nissan Chemical Industries, Ltd.) or OPTMER (registered trademark, manufactured by JSR Corporation), and the like.

When such an alignment film is used, it is unnecessary to control the refractive index by stretching, so that in-plane variation of birefringence becomes small. Therefore, an effect that a large retardation film capable of coping with enlargement of the flat panel display (FPD) device on the supporting substrate can be provided is exhibited.

As a method for forming an alignment film on the supporting substrate, for example, a commercially available alignment film material or a compound which is a material for the alignment film is applied as a solution to the supporting substrate and then annealed, whereby an alignment film can be formed on the supporting substrate.

The thickness of the alignment film thus obtained is, for example, 10 nm to 10000 nm, and preferably 10 nm to 1000 nm. Within the above range, the compound (A) of the present invention, the polymerizable liquid crystal compound (B) and the like can be oriented at a desired angle on the alignment film.

Further, rubbing or polarized UV irradiation can be performed on these alignment films as necessary. By forming the alignment films, the compound (A) of the present invention, the polymerizable liquid crystal compound (B) and the like can be oriented in a desired direction.

As a method for rubbing an alignment film, for example, a method of bringing a rotating rubbing roll around which a rubbing cloth is wound into contact with an alignment film being placed on a stage and conveyed can be used.

As described above, in the step of preparing an unpolymerized film, an unpolymerized film (liquid crystal layer) may be laminated on an alignment film laminated on an arbitrary supporting substrate. In this case, the production cost can be reduced as compared with a method of preparing a liquid crystal cell and injecting a liquid crystal composition into the liquid crystal cell. Furthermore, film production with a roll film is possible.

Drying of the solvent may be carried out while advancing polymerization, and it is preferable to dry most of the solvent before polymerization from the viewpoint of film formability.

Examples of a drying method of the solvent include methods such as natural drying, air drying and vacuum drying. The specific heating temperature is preferably 10 to 120° C., and further preferably 25 to 80° C. Also, the heating time is preferably from 10 seconds to 60 minutes, and more preferably from 30 seconds to 30 minutes. As long as the heating temperature and the heating time are within the above ranges, a supporting substrate which is not necessarily sufficient in heat resistance can be used as the supporting substrate.

Next, the unpolymerized film obtained above is polymerized and cured. Whereby, a film in which the alignment of the compound (A) of the present invention and the polymerizable liquid crystal compound (B) is fixed, that is, a film containing a polymer (cured product) of the liquid crystal composition of the present invention (hereinafter, also referred to as "polymerized film").

The method of polymerizing an unpolymerized film is determined according to the types of the compound (A) of the present invention and the polymerizable liquid crystal compound (B). The unpolymerized film can be polymerized, by photopolymerization in the case where the polymerizable group contained in the polymerizable liquid crystal compound (B) and optionally the compound (A) of the present invention is photopolymerizable, or by thermal polymerization in the case where the polymerizable group is thermopolymerizable. In the present invention, it is particularly preferable to polymerize the unpolymerized film by photopolymerization. According to photopolymerization, the unpolymerized film can be polymerized at low temperature, thus the selection range of heat resistance of the supporting substrate is expanded. Further, photopolymerization also industrially facilitates production. Photopolymerization is also preferred from the viewpoint of film formability. Photopolymerization is carried out by irradiating the unpolymerized film with visible light, ultraviolet light or laser light. From the viewpoint of ease of handling, light irradiation, which is particularly preferably ultraviolet light, may be carried out, while heating to a temperature at which the polymerizable liquid crystal compound (B) takes a liquid crystal phase. At this time, the polymerized film can be also patterned by masking or the like.

Furthermore, the retardation film of the present invention is a thin film as compared with a stretched film which gives retardation by stretching a polymer.

In the method for producing a retardation film of the present invention, a step of peeling the supporting substrate may further be included. With such a constitution, the obtained laminate becomes a film comprising an alignment film and a retardation film. Further, in addition to the step of peeling the supporting substrate, a step of peeling the alignment film may be further included. By adopting such a constitution, a retardation film can be obtained.

EXAMPLES

Hereinafter, the present invention will be specifically described with reference to Examples and Comparative Examples, but the present invention is not limited to these Examples. In the examples, "%" and "parts" mean mass % and parts by mass, unless otherwise specified.

[HPLC Measurement]

The HPLC measurement may be carried out under any conditions as long as peaks derived from the compound (A) and the polymerizable liquid crystal compound (B) can be separated. An example of HPLC measurement conditions is shown below.

(Measurement Conditions)

Measuring device: HPLC LC-10AT (manufactured by Shimadzu Corporation)

Column: L-Column ODS (inner diameter 3.0 mm, length 150 mm, particle diameter 3 μm)

Temperature: 40° C.

Mobile phase A: 0.1% (v/v)-TFA/water

Mobile phase B: 0.1% (v/v)-TFA/acetonitrile

Gradient: 0 min 70%-B 30 min 100%-B 60 min 100%-B 60.01 min 70%-B 75 min 70%-B

Flow rate: 0.5 mL/min

Injection volume: 5 μL

Detection wavelength: 254 nm

Example 1: Preparation of Compound Represented by Formulas (A-1) and (A-2)

A compound represented by following formula (A-1) (hereinafter referred to as "compound (A-1)") and a compound represented by following formula (A-2) (hereinafter referred to as "compound (A-2)") were synthesized according to the following scheme.

[Chemical Formula 25]

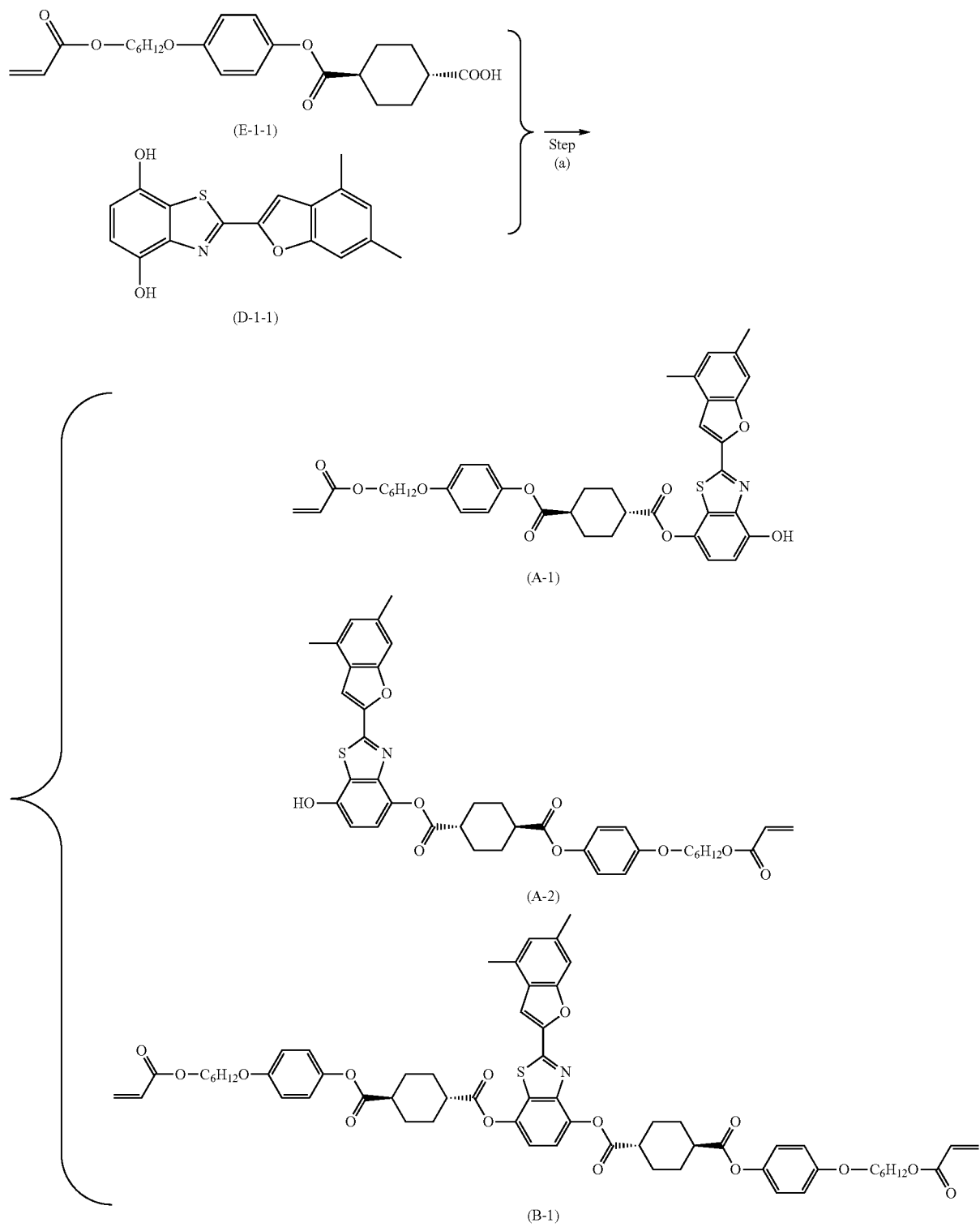

<Step (a)>

The inside of a 100 mL four-necked flask equipped with a Dimroth condenser and a thermometer was converted into nitrogen atmosphere, and 8.06 g of compound (E-1-1) synthesized with reference to Patent Document (JP-A-2010-31223), 4.00 g of compound (D-1-1) synthesized with reference to Patent Document (JP-A-2011-207765), 0.02 g of dimethylaminopyridine (hereinafter abbreviated as "DMAP", manufactured by Wako Pure Chemical Industries, Ltd.), 0.20 g of dibutylhydroxytoluene (hereinafter abbreviated as "BHT", manufactured by Wako Pure Chemical Industries, Ltd.), and 40 g of chloroform (manufactured by Kanto Chemical Co.) were mixed, then 2.11 g of diisopropylcarbodiimide (hereinafter abbreviated as "IPC", manufactured by Wako Pure Chemical Industries, Ltd.) was further added using a dropping funnel, and the mixture was reacted at 0° C. overnight.

After completion of the reaction, insoluble components were removed by filtration. From the resulting chloroform solution, the solvent was distilled off using a rotary evaporator, and 20 g of acetonitrile (manufactured by Wako Pure Chemical Industries, Ltd.) was added dropwise to the solution after the distillation to precipitate a solid. Subsequently, the precipitated solid was taken out by filtration and washed three times with 20 g of acetonitrile, then dried under reduced pressure at 30° C. to obtain 6.46 g of a composition (A'). As a result of analyzing the resulting composition (A') by HPLC measurement, the composition contained the above compounds (A-1), (A-2) and (B-1), and the total amount of the compound (A-1) and the compound (A-2) was 20.21% based on 100% of the total of the compounds (A-1), (A-2) and (B-1).

As a result of analyzing the composition (A') under the HPLC measurement conditions as described above, Compound 1 was obtained at a retention time of 19.4 minutes, and Compound 2 was obtained at a retention time of 20.9 minutes. The respective molecular weights of Compounds 1 and 2 were measured by LC/MS analysis, and it was found that both molecular weights were 711.83. From this result and the above reaction scheme, it was identified that Compounds 1 and 2 contained in the composition (A') were the above compounds (A-1) and (A-2).

Production Example 1: Preparation of Compound Represented by Formula (B-1)

A polymerizable liquid crystal compound represented by following formula (B-1) (hereinafter referred to as "compound (B-1)") was synthesized according to the following scheme.

[Chemical Formula 26]

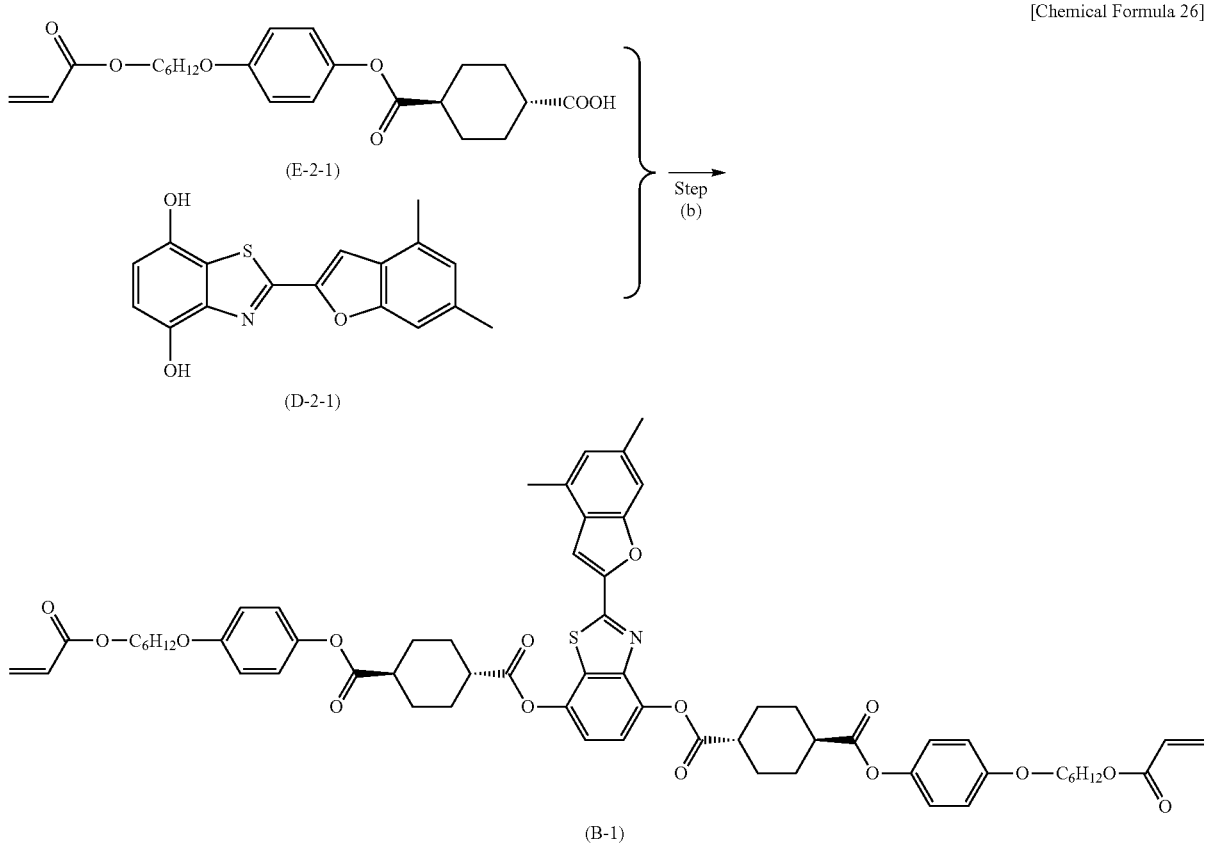

<Step (b)>

The inside of a 100 mL four-necked flask equipped with a Dimroth condenser and a thermometer was converted into nitrogen atmosphere, and 11.02 g of compound (E-2-1) synthesized with reference to Patent Document (JP-A-2010-31223), 4.00 g of compound (D-2-1) synthesized with reference to Patent Document (JP-A-2011-207765), 0.02 g of DMAP (manufactured by Wako Pure Chemical Industries, Ltd.), 0.20 g of BHT (manufactured by Wako Pure Chemical Industries, Ltd.), and 58 g of chloroform (manufactured by Kanto Chemical Co.) were mixed, then 4.05 g of IPC (manufactured by Wako Pure Chemical Industries, Ltd.) was further added using a dropping funnel, and the mixture was reacted at 0° C. overnight. After completion of the reaction, insoluble components were removed by filtration. The resulting chloroform solution was added dropwise to acetonitrile (manufactured by Wako Pure Chemical Industries, Ltd.) having three times the weight of the chloroform contained in the solution to precipitate a solid. Subsequently, the precipitated solid was taken out by filtration and washed three times with 20 g of acetonitrile, and dried under reduced pressure at 30° C. to obtain 11.43 g of a compound (B-1).

The yield of the compound (B-1) was 80% based on the compound (D-2-1). The maximum absorption wavelength ($\lambda_{max}$) of the polymerizable liquid crystal compound (B-1) was 352 nm.

$^1$H-NMR (CDCl$_3$) of the compound (B-1): δ (ppm) 1.45 to 1.85 (m, 24H), 2.36 to 2.87 (m, 18H), 3.93 to 3.97 (t, 4H), 4.15 to 4.20 (t, 4H), 5.79 to 5.84 (dd, 2H), 6.07 to 6.17 (m, 2H), 6.37 to 6.45 (m, 2H), 6.87 to 7.01 (m, 9H), 7.20 (s, 1H), 7.23 (s, 2H), 7.53 (s, 1H)

Example 2: Production of Liquid Crystal Composition (1)

5 mg of the composition (A') containing the compounds (A-1), (A-2) and (B-1) obtained in Example 1 and 995 mg of the polymerizable liquid crystal compound (B-1) obtained in Production Example 1 were mixed to obtain a liquid crystal composition (1). HPLC analysis was performed using the resulting liquid crystal composition (1) under the above measurement conditions to measure the area percentage value of the compounds (A-1) and (A-2) based on the total amount of the compounds (A-1), (A-2) and (B-1).

Examples 3 and 4: Production of Liquid Crystal Compositions (2) and (3)

Liquid crystal compositions (2) and (3) were obtained in the same manner as in Example 2 except that the mixing ratio of the compound (A') obtained in Example 1 and the polymerizable liquid crystal compound (B-1) was each changed as shown in Table 1.

Comparative Example 1

The polymerizable liquid crystal compound (B-1) obtained in Production Example 1 was designated as Comparative Example 1.

Comparative Example 2

The composition (A') obtained in Example 1 was designated as Comparative Example 2.
[Measurement of Nematic Phase Transition Temperature]

1000 mg of the composition of Example 2 was weighed in a vial tube and dissolved by further adding 2 g of chloroform thereto. The resulting solution was applied to a glass substrate with a rubbed PVA alignment film and dried. The substrate was placed on a cooling and heating device ("LNP94-2" manufactured by JAPAN HIGH TECH CO., LTD.), and the temperature was raised from room temperature to 180° C. and then cooled to room temperature. The state at a time of temperature change was observed with a polarizing microscope (LEXT, manufactured by OLYMPUS CORPORATION), and the temperature at which a nematic phase was formed was measured and taken as the nematic phase transition temperature. The nematic phase transition temperature was measured in the same manner for the compositions of Examples 3 and 4 and Comparative Examples 1 and 2. The obtained results are shown in Table 1.

TABLE 1

| Composition | Mixing ratio (B-1) [mg] | Mixing ratio (A') [mg] | Area percentage values of (A-1) and (A-2) [%] | Nematic phase transition temperature [° C.] |
|---|---|---|---|---|
| Example 2 | 995 | 5 | 0.10 | 148 |
| Example 3 | 951 | 49 | 1.00 | 148 |
| Example 4 | 505 | 495 | 10.00 | 144 |
| Comparative Example 1 | 1000 | 0 | 0.00 | 156 |
| Comparative Example 2 | 0 | 1000 | 20.21 | 143 |

[Preparation of Composition for Forming Photo-Alignment Film]

The following components were mixed, and the resulting mixture was stirred at 80° C. for 1 hour to obtain a composition for forming a photo-alignment film.

Photo-alignment material (5 parts) represented by the following formula:

[Chemical Formula 27]

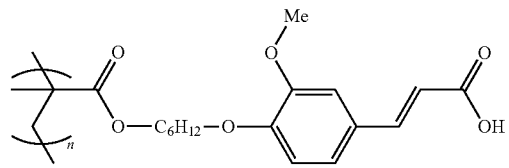

Solvent (95 parts): Cyclopentanone
[Production of Optical Film (Retardation Film)]

An optical film was produced as follows. A cycloolefin polymer film (COP) (ZF-14, manufactured by Zeon Corporation) was treated in the conditions of an output of 0.3 kW and a treatment rate of 3 m/min, using a corona treatment generator (AGF-B10, manufactured by KASUGA DENKI, Inc.). The composition for forming a photo-alignment film was applied to the corona-treated surface using a bar coater, dried at 80° C. for 1 minute, and polarized UV exposure was performed with an integrated light amount of 100 mJ/cm$^2$ with a polarized UV irradiation device (SPOT CURE SP-7, manufactured by USHIO INC.). The film thickness of the resulting alignment film was measured with a laser microscope (LEXT, manufactured by Olympus Corporation) and found to be 100 nm.

Subsequently, the liquid crystal composition (1) obtained in Example 2 was charged into a vial tube, and a polymerization initiator, a leveling agent, a polymerization inhibitor and a solvent were charged in accordance with the composition shown in Table 2, and the mixture was stirred at 80° C. for 30 minutes using a carousel to obtain a liquid crystal composition-containing mixed solution (1).

The amounts of the polymerization initiator, the leveling agent and the polymerization inhibitor shown in Table 2 are those charged to 100 parts by mass of the liquid crystal composition (1) obtained in Example 2. In addition, the blending amount of the solvent was set so that the % by mass of the liquid crystal composition (1) was 13% based on the total amount of the solution.

TABLE 2

|  | Polymerization initiator | Leveling agent | Polymerization inhibitor |
|---|---|---|---|
| Addition amount [Parts by mass] | 6.0 | 0.1 | 0.2 |

Polymerization Initiator:
2-Benzyl-2-dimethylamino-1-(4-morpholinophenyl)butan-1-one (Irgacure 369; manufactured by BASF Japan)
Leveling agent: Polyacrylate compound (BYK-361N; manufactured by BYK Japan KK)
Polymerization inhibitor: BHT (manufactured by Wako Pure Chemical Industries, Ltd.)
Solvent: N-methylpyrrolidone (NMP; manufactured by Kanto Chemical Co.)

The resulting liquid crystal composition-containing mixed solution (1) was applied to the alignment film using a bar coater, dried at 120° C. for 1 minute, and then irradiated with ultraviolet light (under a nitrogen atmosphere, wavelength: 365 nm, cumulative light amount at a wavelength of 365 nm: 1000 mJ/cm$^2$) using a high pressure mercury lamp (Unicure VB-15201BY-A, manufactured by USHIO INC.) to prepare an optical film (1).

Optical films (2) to (5) were prepared in the same manner as above except that the compositions of Examples 3 and 4 and Comparative Examples 1 and 2 were respectively used in place of the liquid crystal composition (1).

[Evaluation of Alignment Defect]
The resulting optical film was cut into 10 cm square, and the number of alignment defects on the screen was visually confirmed using a polarizing microscope (LEXT, manufactured by Olympus Corporation) and evaluated according to the following evaluation criteria. The results are shown in Table 3.
(Evaluation Standard of Alignment Defect)
 1: Alignment defects occur on the entire surface (>100)
 2: 11 to 100 alignment defects
 3: 1 to 10 alignment defects
 4: No defect

[Measurement of Optical Characteristic Re(450)/Re(550)]
Using the optical film prepared above as a measurement sample, the front retardation value for light at a wavelength of 450 nm and a wavelength of 550 nm was measured using a measuring machine ("KOBRA-WR" manufactured by Oji Scientific Instruments), and Re(450)/Re(550) was calculated. The obtained results are shown in Table 3.

TABLE 3

| Optical film | Composition | Alignment defect | Re(450)/Re(550) |
|---|---|---|---|
| (1) | Example 2 | 4 | 0.82 |
| (2) | Example 3 | 4 | 0.82 |
| (3) | Example 4 | 4 | 0.82 |
| (4) | Comparative Example 1 | 4 | 0.82 |
| (5) | Comparative Example 2 | 1 | 0.83 |

As shown in Table 1, the liquid crystal compositions of Examples 2 to 4 of the present invention had a reduced nematic phase transition temperature by including the compound (A) obtained in Example 1. Further, in the optical films (1) to (3) obtained from the liquid crystal compositions of Examples 2 to 4, alignment defect was not observed as shown in Table 3. Further, the value of Re(450)/Re(550) satisfies the formula (1): 0.80≤Re(450)/Re(550)<1.00, and no adverse effect on reverse wavelength dispersibility by adding the compound of Example 1 was observed.

On the other hand, in the composition of Comparative Example 1 not containing the compound (A) obtained in Example 1, while no alignment defect was observed in the resulting optical film, the composition had a high nematic phase transition temperature. In addition, in the composition of Comparative Example 2 containing the compound (A) obtained in Example 1 in an amount exceeding a predetermined amount, while a drop in the nematic phase transition temperature was observed, alignment defects occurred in the resulting optical film. From these results, it was confirmed that by adding the compound of the present invention in a predetermined amount, alignment defects are suppressed and also the phase transition temperature can be lowered without preventing the alignment of the liquid crystal compound too much, and drying temperature when forming a film can be lowered while maintaining reverse wavelength dispersibility.

What is claimed is:
1. A liquid crystal composition comprising at least one photopolymerization initiator, at least one compound represented by the formula (A), and at least one polymerizable liquid crystal compound represented by formula (B), wherein the area percentage value of the at least one compound represented by the formula (A) as measured by liquid chromatography is 0.05 to 18% based on the sum of area values of the at least one compound represented by the formula (A) and the at least one polymerizable liquid crystal compound represented by the formula (B) contained in the liquid crystal composition:

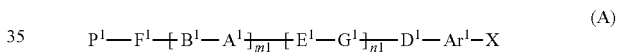

$$P^1-F^1\!-\!\!\left[\!B^1\!-\!A^1\right]_{\!m1}\!\!-\!\!\left[\!E^1\!-\!G^1\right]_{\!n1}\!\!-\!D^1\!-\!Ar^1\!-\!X \quad (A)$$

wherein $B^1$, $E^1$ and $D^1$ each independently represent a single bond or a divalent linking group, $A^1$ and $G^1$ each independently represent a divalent aromatic hydrocarbon group having 6 to 20 carbon atoms or a divalent alicyclic hydrocarbon group having 3 to 16 carbon atoms, the hydrogen atoms contained in the aromatic hydrocarbon group or the alicyclic hydrocarbon group may each independently be substituted with a halogen atom, —$R^1$, —$OR^1$, a cyano group or a nitro group, $R^1$ represents an alkyl group having 1 to 4 carbon atoms, the hydrogen atoms contained in the alkyl group may each independently be substituted with a fluorine atom, the carbon atoms contained in the aromatic hydrocarbon group or the alicyclic hydrocarbon group may each independently be substituted with an oxygen atom, a sulfur atom or a nitrogen atom, $F^1$ represents an alkanediyl group having 1 to 17 carbon atoms, the hydrogen atoms contained in the alkanediyl group may each independently be substituted with a halogen atom, —$R^1$ or —$OR^1$, $R^1$ has the same meaning as described above, —$CH_2$— contained in the alkanediyl group may each independently be substituted with —O—, —S—, —Si— or —CO—, m1 and n1 each independently represent an integer of 0 to 3, $Ar^1$ is a divalent aromatic group which may have a substituent, and contains at least one atom selected from the group consisting of a nitrogen atom, an oxygen atom and a sulfur atom, in the aromatic group, $P^1$ represents a polymerizable group, X represents —OH, —SH, —C(=O)OH, —C(=S)OH, —$NR^2$H or —$(CH_2)_p$—OH, $R^2$ represents a hydrogen atom or an alkyl group having 1 to 4 carbon atoms, and p represents an integer of 1 to 3;

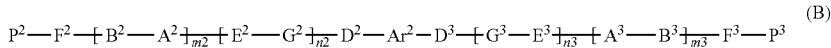

wherein $B^2$, $B^3$, $E^2$, $E^3$, $D^2$ and $D^3$ each independently represent a single bond or a divalent linking group, $A^2$, $A^3$, $G^2$ and $G^3$ each independently represent a divalent aromatic hydrocarbon group having 6 to 20 carbon atoms or a divalent alicyclic hydrocarbon group having 3 to 16 carbon atoms, the hydrogen atoms contained in the aromatic hydrocarbon group or the alicyclic hydrocarbon group may each independently be substituted with a halogen atom, —$R^1$, —$OR^1$, a cyano group or a nitro group, $R^1$ has the same meaning as described above, the carbon atoms contained in the aromatic hydrocarbon group or the alicyclic hydrocarbon group may each independently be substituted with an oxygen atom, a sulfur atom or a nitrogen atom, $F^2$ and $F^3$ each independently represent an alkanediyl group having 1 to 17 carbon atoms, the hydrogen atoms contained in the alkanediyl group may each independently be substituted with a halogen atom, —$R^1$ or —$OR^1$, $R^1$ has the same meaning as described above, —$CH_2$— contained in the alkanediyl group may each independently be substituted with —O—, —S—, —Si— or —CO—, m2, m3, n2 and n3 each independently represent an integer of 0 to 3, $Ar^2$ is a divalent aromatic group which may have a substituent, and contains at least one atom selected from the group consisting of a nitrogen atom, an oxygen atom and a sulfur atom, in the aromatic group, $P^2$ and $P^3$ each independently represent a polymerizable group.

2. The compound according to claim 1, wherein $G^1$ is a trans-cyclohexane-1,4-diyl group.

3. The compound according to claim 1, wherein $D^1$ is a group represented by formula (C)

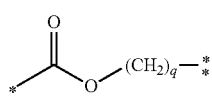

wherein * represents a linking moiety with $G^1$, ** represents a linking moiety with $Ar^1$, and q represents an integer of 0 to 3.

4. The compound according to claim 1, wherein X is —OH or —$(CH_2)_p$—OH.

5. The compound according to claim 1, wherein m1 and n1 are 1.

6. The compound according to claim 1, wherein $B^1$, $E^1$ and $D^1$ each independently represent a single bond, —$CR^3R^4$—, —$(CH_2)_r$—, —O—, —S—, —CO—O—, —O—CO—, —CO—O—$(CH_2)_r$—, —$(CH_2)_r$—O—CO—, —O—CO—O—, —C(=S)—O—, —O—C(=S)—, —O—C(=S)—O—, —CO—$NR^3$—, —$NR^3$—CO—, —O—$CH_2$—, —$CH_2$—O—, —S—$CH_2$— or —$CH_2$—S—, $R^3$ and $R^4$ each independently represent a hydrogen atom, a fluorine atom or an alkyl group having 1 to 4 carbon atoms, and r represents an integer of 1 to 4.

7. The liquid crystal composition according to claim 1, wherein, in the formula (A) and the formula (B), $B^1$ and $B^2$ and $B^3$ are the same, $E^1$ and $E^2$ and $E^3$ are the same, $D^1$ and $D^2$ and $D^3$ are the same, $A^1$ and $A^2$ and $A^3$ are the same, $G^1$ and $G^2$ and $G^3$ are the same, $F^1$ and $F^2$ and $F^3$ are the same, m1 and m2 and m3 are the same, n1 and n2 and n3 are the same, $Ar^1$ and $Ar^e$ are the same, and $P^1$ and $P^2$ and $P^3$ are the same.

8. A layer containing a cured product of the liquid crystal composition as defined in claim 1.

9. An optical film having at least the layer as defined in claim 8.

10. The optical film according to claim 9, which is a retardation film.

11. The optical film according to claim 10, which satisfies following formula (I):

$$0.80 \leq Re(450)/Re(550) < 1.00 \quad (I)$$

wherein Re represents a front retardation value for light at a wavelength of λ nm.

12. A polarizing plate comprising the optical film as defined in claim 9.

13. An optical display comprising the polarizing plate as defined in claim 12.

* * * * *